United States Patent
Urakawa et al.

(10) Patent No.: US 7,414,791 B2
(45) Date of Patent: Aug. 19, 2008

(54) EYE DETECTION APPARATUS AND IMAGE DISPLAY APPARATUS

(75) Inventors: Takashi Urakawa, Yokohama (JP); Yoshihiroi Saito, Hachioji (JP); Akinari Takagi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 440 days.

(21) Appl. No.: 11/245,896

(22) Filed: Oct. 6, 2005

(65) Prior Publication Data

US 2006/0077558 A1    Apr. 13, 2006

(30) Foreign Application Priority Data

Oct. 8, 2004    (JP)    ............... 2004-295869

(51) Int. Cl.
  *G02B 27/14*    (2006.01)
  *G02B 3/02*     (2006.01)
  *A61B 3/10*     (2006.01)
  *H04N 5/262*    (2006.01)

(52) U.S. Cl. .............. 359/630; 359/708; 351/205; 348/239

(58) Field of Classification Search ......... 359/630, 359/708; 348/239, 173, 190, 286; 351/205, 351/206
See application file for complete search history.

(56) References Cited

U.S. PATENT DOCUMENTS

| | | | |
|---|---|---|---|
| 6,987,535 B1 * | 1/2006 | Matsugu et al. | 348/239 |
| 7,324,669 B2 * | 1/2008 | Nakanishi et al. | 382/118 |
| 2005/0117802 A1 * | 6/2005 | Yonaha et al. | 382/173 |
| 2006/0077344 A1 * | 4/2006 | Kashiwagi et al. | 351/206 |

FOREIGN PATENT DOCUMENTS

| | | |
|---|---|---|
| JP | 5-66340 | 3/1993 |
| JP | 6-276459 | 9/1994 |
| JP | 2001-142026 | 5/2001 |

\* cited by examiner

*Primary Examiner*—Mohammed Hasan
(74) *Attorney, Agent, or Firm*—Morgan & Finnegan, L.L.P.

(57) ABSTRACT

What is disclosed is an eye detection apparatus which can detect the pupil position accurately. The apparatus has an image taking unit that picks up an image of an eye and a pupil detection unit that detects the position of the pupil in the eye based on an image picked up by the image taking portion. The pupil detection unit determines the pupil position based on images picked up by the image taking unit in a plurality of states.

10 Claims, 19 Drawing Sheets

EYE DETECTION APPARATUS AND IMAGE DISPLAY APPARATUS

BACKGROUND OF THE INVENTION

1. Field of the Invention

The present invention relates to an eye detection apparatus provided in, for example, a head mount display to be mounted on the head of a user, for detecting the position of a pupil of the user.

2. Description of Related Art

When an observer wears a head mounted display (which will be abbreviated as HMD hereinafter) and observes an image, if the designed optical axis of the display optical system and the direction of the line of sight of the observer do not coincide with each other, there is a possibility that when the observer moves his/her eye to observe a peripheral portion of the image, the eye deviates from the pupil diameter of the display optical system to cause eclipse or spoil strength of observed images, though it is possible to observe the central portion of the image.

To make the HMD suitable for an increased number of observers, it is necessary to make the pupil diameter of the display optical system larger. However, the size of the display optical system will increase with the increase in the pupil diameter.

There are technologies for detecting the position of a pupil or the direction of the line of sight of an observer, such as a technology in which an eye is irradiated with several infrared rays (IR) and the direction of the line of sight is detected based on the reflected rays and Purkinje images (see, for example, Japanese Patent Application Laid-Open No. H05-66340, Japanese Patent Application Laid-Open No. H06-276459 and Japanese Patent Application Laid-Open No. 2001-142026).

In this method, it is required that the reflected IR rays to be detected be within the area of the colored part of the eye, and it is necessary that the position of the eye of the observer be in a limited small area (a predetermined area) relative to the HMD. In connection with detecting the direction of the line of sight, to detect Purkinje images, it is necessary to move the eye to left and right over an angle range of about 15 degrees.

However, the observer does not necessarily always wear the HMD in the same position. In addition, when the observer wears the HMD, the position of an eye of the observer relative to the HMD is not always in the aforementioned predetermined area. In cases where the position of the eye is not in the predetermined area, the position of the pupil of the observer cannot be detected accurately using the aforementioned conventional detecting method.

Moreover, while there is a trend of widening the angle of field of the HMD recently, the above-described conventional detection method cannot cope with the widening of the angle of view, since its detection area is limited.

SUMMARY OF THE INVENTION

An eye detection apparatus that exemplifies the present invention comprises an image taking unit that picks up an image of an eye and a pupil detection unit that detects the position of the pupil in the eye based on a picked up image obtained by the image taking unit, wherein the image taking unit determines the pupil position based on picked up images obtained in a plurality of states by the image taking unit.

DETAILED DESCRIPTION OF THE PREFERRED EMBODIMENTS

In the following, embodiments of the present invention will be described.

First Embodiment

Figure 1A:
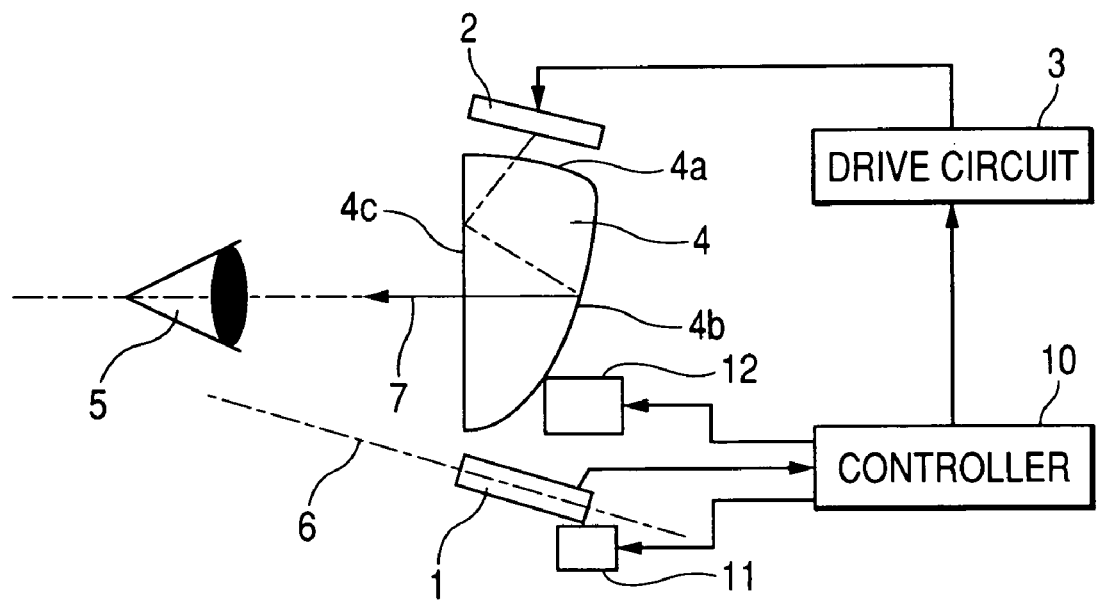
FIG. 1A is a side view schematically showing the structure of an HMD according to a first embodiment of the present invention.
Figure 1B:
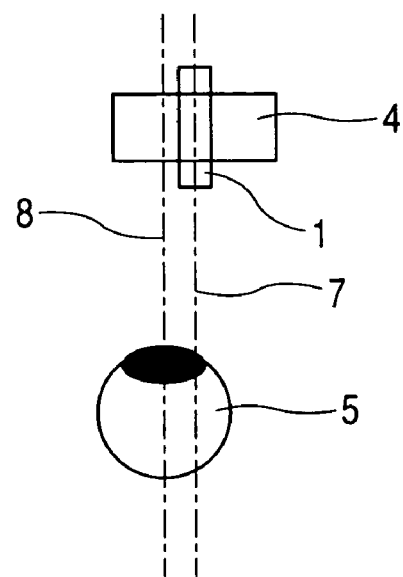
FIG. 1B is a top view thereof.

An image display apparatus (HMD) according to the first embodiment of the present invention will be described. FIG. 1A is a side view schematically showing the inner structure of the HMD according to this embodiment. FIG. 1B is a top view of the inner structure.

In the HMD of this embodiment, as shown in FIG. 1B, the optical axis of an image taking unit and the optical axis of a display optical system are in the same plane, and horizontal displacement (displacement in the right-and-left direction in FIG. 1B) of the optical axis position (or the position of the emerging optical axis) of the display optical system relative to the position of a pupil (or the position of the line of sight) of the observer is to be detected.

Reference numeral 1 designates an image taking unit which has an image pickup element such as a CCD sensor or a CMOS sensor and an optical system for forming an image of an eye of an observer on the image pickup element. Reference numeral 2 designates an image forming element (display unit) such as an LCD, an LCOS, an EL or a scanning system. Reference numeral 3 designates a drive circuit that supplies the image forming element 2 with image signals. Reference numeral 4 designates a display optical system for enlarging a displayed image on the image forming element 2, the display optical system 4 being composed of a free form surface prism or the like.

Reference numeral 5 designates an eye (or an eyeball) of the observer who wears the HMD to observe an image. Reference numeral 6 designates the optical axis of the image taking unit 1, and reference numeral 7 designates the emerging optical axis (shown as a solid line) of the display optical system 4. As shown in FIG. 1B, the image taking unit 1 and the display optical system 4 are disposed in such a way that the optical axis 6 of the image taking unit 1 and the emerging optical axis 7 of the display optical system 4 are in the same plane. Reference numeral 8 designates the line of sight of the observer.

Reference numeral 10 designates a controller (a pupil detection unit) that controls operations of the HMD. Reference numeral 11 designates a first drive unit (a drive unit), which receives a command from the controller 10 and moves the image taking unit 1 in the left and right directions in FIG. 1A (in the up and down directions in FIG. 1B). Reference numeral 12 designates a second drive unit (drive unit), which receives a command from the controller 10 and moves the display optical system 4 in the left and right directions (horizontal direction) in FIG. 1B. The first drive unit 11 and the second drive unit 12 are mechanically linked with the image taking unit 1 and the display optical system 4 respectively.

In the above described structure, an image formed on the image forming element 2 is transmitted through the first surface 4a of the display optical system 7, reflected by the second surface 4b and the third surface 4c, and emerging from the fourth surface 4d, as shown in FIG. 1A. Thus, light from the image forming element 2 is guided to the eye 5 of the observer.

The typical diameter of the colored part (or the iris) of a human eye is approximately 10 mm. In this embodiment, the design value of the eye relief of the display optical system 4 is 20 mm, and the image taking unit 1 is disposed outside the display optical system 4 and on the center axis of the display optical system 4 with respect to the horizontal direction as shown in FIG. 1B. If the horizontal image taking range at a distance of 20 mm from the display optical system 4 is set to 20 mm, the image taking unit 1 can pick up an image of the whole eye even if the position of the pupil of the observer who wears the HMD is displaced from the design value horizontally by ±5 mm.

In the HMD of this embodiment, when the observer wears the HMD and depresses a measurement start button (not shown) provided on the HMD, the eye 5 of the observer is irradiated with illumination light. The system is adapted in such a way that light reflected from the eye 5 enters the image taking unit 1, and an operation of picking up a reflection image is performed by the image taking unit 1.

Since irradiation of the eye 5 of the observer with visible illumination light is sometimes annoying to the observer, infrared light outside the visible region is used as illumination light in this embodiment.

When an image of the eye of the observer is to be picked up, it is necessary that the emerging optical axis 7 of the display optical system 4 and the line of sight 8 of the observer be substantially parallel to each other as shown in FIG. 1B. In the case where the emerging optical axis 7 and the line of sight 8 are not substantially parallel, a displacement will remain, as will be described later, even if the display optical system 4 is moved in such a way that the position of the emerging optical axis 7 (which position will be hereinafter referred to as the optical axis position) of the display optical system 4 coincides with the detected position of the pupil of the observer.

Figure 2:
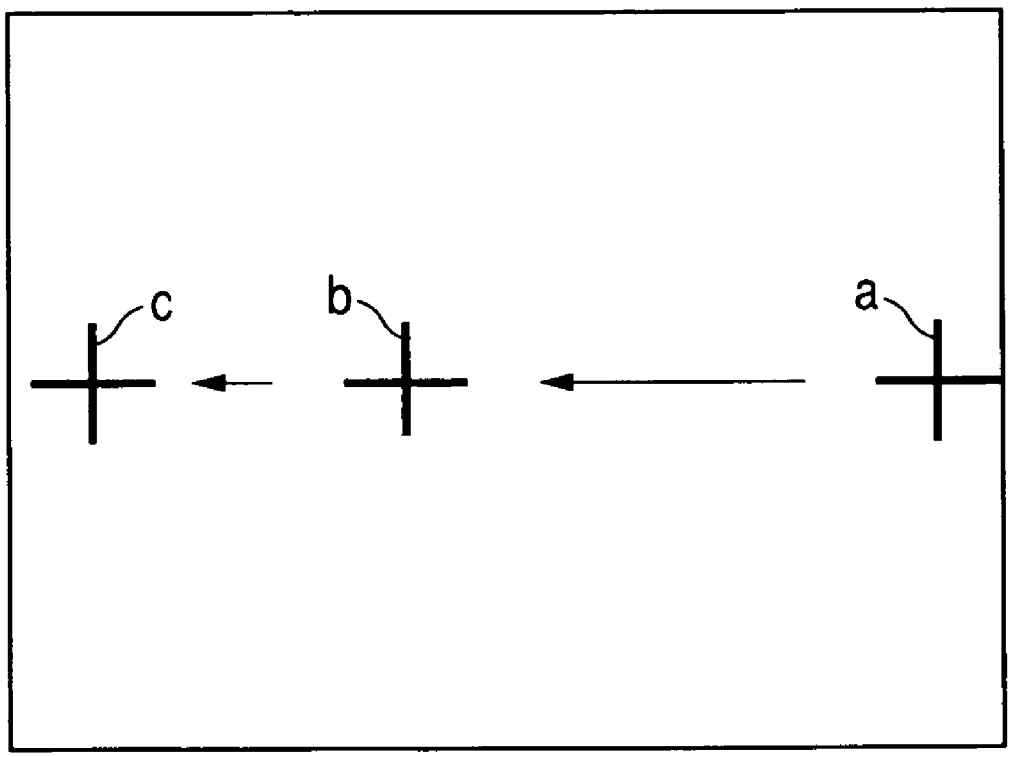
FIG. 2 illustrates how an index is displayed in the HMD according to the first embodiment.

When the aforementioned measurement start button is depressed, a cross-shaped index is displayed at the right end a of the display area of the image forming element 2 as shown in FIG. 2. The index is moved in the direction indicated by the arrows in FIG. 2 from position a by small steps. For example, the index is displayed at position b and position c in the mentioned order.

Thus, the observer is instructed to follow the index with his/her eye. While the observer follows the index with his/her eye, an image of the eye is sequentially picked up (at every position of the index displayed) by the image taking unit 1. The aforementioned index may be displayed as a motion picture. The direction of movement of the index may be opposite to that indicated by the arrows in FIG. 2.

Figure 3A:
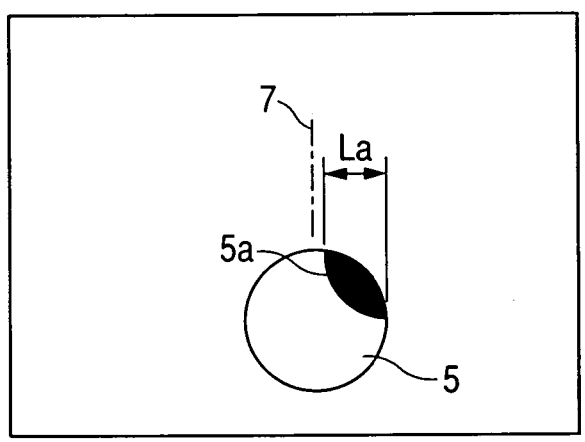
FIGS. 3A, 3B and 3C illustrate observing states of an eye in the first embodiment.
Figure 3B:
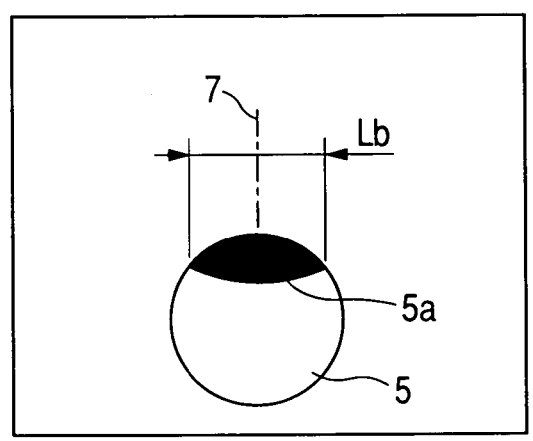
Figure 3C:
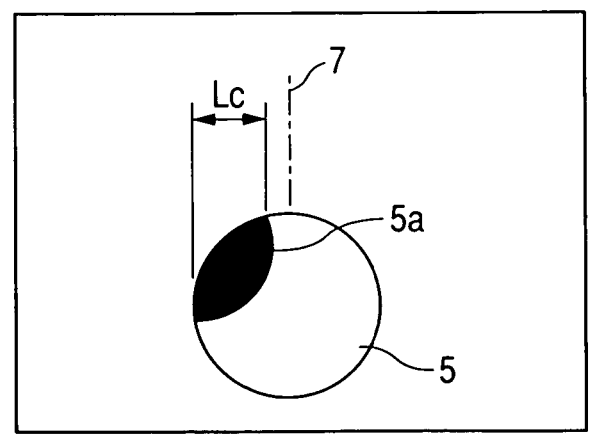

FIGS. 3A to 3C show states of the eye 5 while following the index.

In the state in which the eye 5 of the observer is tilted to one of the left and right directions (horizontal directions), in other words, in the state in which the line of sight 8 of the observer is not substantially parallel to the emerging optical axis 7 of the display optical system 4 but inclined to it, the horizontal length (or width) (in the direction orthogonal to the emerging optical axis 7 of the colored part 5a of the eye 5 is La shown in FIG. 3A.

On the other hand, in the state in which the line of sight 8 of the observer is substantially parallel to the emerging optical axis 7 of the display optical system 4, the horizontal length (or width) of the colored part 5a of the eye 5 is Lb shown in FIG. 3B.

In the state in which the eye 5 is tilted to the other direction, where the line of sight 8 of the observer is not substantially parallel to the emerging optical axis 7 of the display optical system 4 but inclined to it, the horizontal length (or width) of the colored part 5a of the eye 5 is Lc shown in FIG. 3C.

In the states shown in FIGS. 3A and 3C, the line of sight 8 is inclined to the emerging optical axis 7, and therefore lengths La and Lc are shorter than length Lb, namely, length Lb in the state shown in FIG. 3B is the largest.

In this embodiment, the state of the eye 5 shown in FIG. 3B, or the state in which the width of the colored part 5a of the eye 5 becomes the largest, is determined based on multiple image data obtained by successive image pickup operations performed by the image taking unit 1. Then, the index at the position associated with the state shown in FIG. 3B is displayed on the image forming element 2 again. The observer is instructed to see the displayed index again, and an image of the eye 5 while observing is picked up. This state will be referred to as the first state.

Based on the image data obtained by the image pickup operation performed in the first state, both ends of the colored part 5a of the eye are extracted, and the center of them is set as the pupil position. Here, the resolution in detecting the pupil position depends on the resolution of the image pickup element included in the image taking unit 1. For example, if the pupil position is to be detected with 0.1 mm pitch, the horizontal resolution of the image taking unit 1 should be 200 (pixels) or more, since the image pickup range in the horizontal direction is 20 mm as described before.

Figure 4:
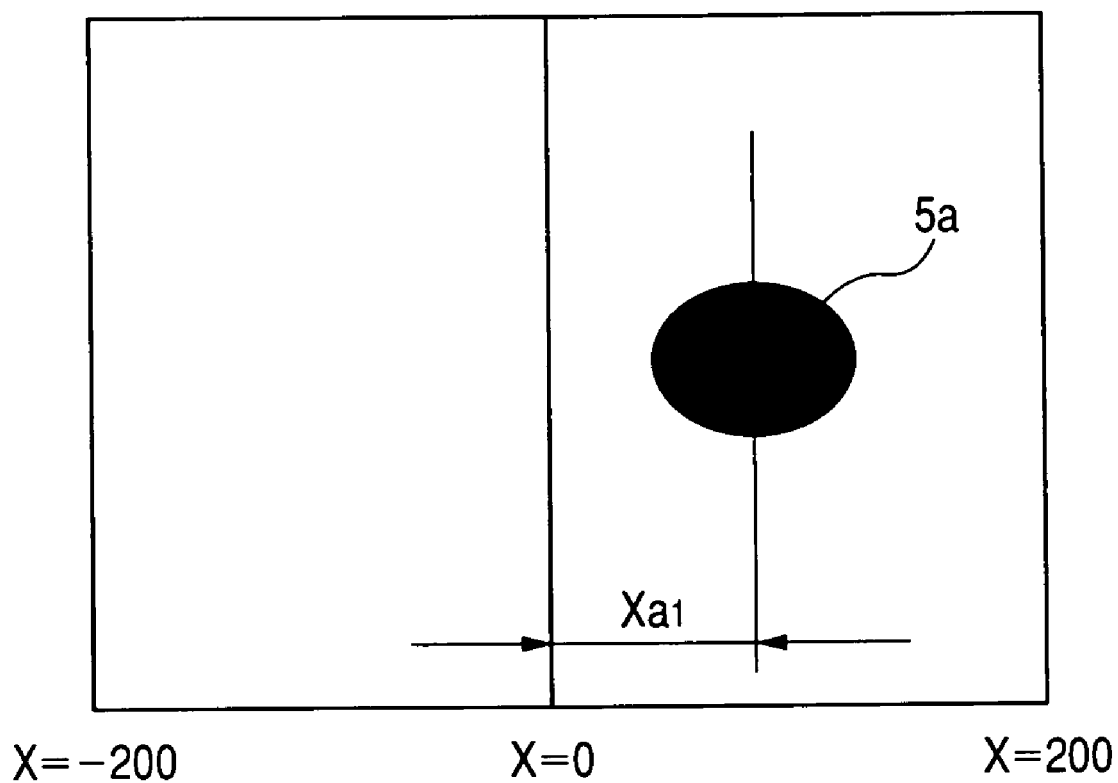
FIG. 4 is a diagram showing a shift amount of the pupil position in the first embodiment.

In this embodiment, it is assumed that the horizontal resolution of the image taking unit 1 is 400. The point of origin (the reference position) is set at the center of the image obtained by the image pickup operation, and the X coordinate is set in the range of ±200 as shown in FIG. 4. In addition, the shift amount in the X direction (horizontal direction) of the pupil position from the point of origin is represented by Xa1.

The shift amount Xa1 can be obtained from formula (1) presented below.

$$X_{a1} = \frac{20 \times (Xcoordinate)}{400} \quad (1)$$

The image of the eye obtained by the image pickup operation is an image under the state in which the eye 5 of the observer is at the position corresponding to the designed value 20 mm of the eye relief. However, the eye of the observer is sometimes not at the desired eye relief position when he/she observes the display optical system 4. In such cases, the picked up image of the eye includes a magnification error (an error in the image pickup magnification), and the pupil position at that time may be displaced from the pupil position with the prescribed eye relief.

Therefore, it is necessary to correct the above-mentioned error (i.e. the magnification error). One method of correcting the magnification error is to move the image taking unit 1 in such a way that the distance between the eye 5 and the image taking unit 1 becomes larger than that before moving the image taking unit 1, in other words, to increase the optical path length as compared to that before moving the image taking unit 1 to enlarge the image pickup area. In the case where it is not possible to move the image taking unit 1 physically, the image pickup magnification may be changed to realize an optical effect equivalent to that realized by moving the image taking unit 1.

In the following, an operation of measuring an actual shift amount (displacement amount) of the pupil position while observing and an operation of driving the display optical system 4 based on that shift amount will be described with reference to FIG. 5. Here, the case where the image taking unit 1 is moved will be described.

In step S1, the controller 10 controls driving of the first drive unit 11 to move the image taking unit 1 in the direction away from the eye 5 by a predetermined amount (here, 10 mm). Thus, the image pickup area of the image taking unit 1 is changed to 40 mm at a distance of 30 mm from the display optical system 4.

In step S2, the controller 10 controls driving of the drive circuit 3 to display the index at the position on the image forming element 2 same as that in the first state to instruct the observer to see the index. This state will be referred to as the second state.

In step S3, an image pickup operation is performed in the second state. A signal read out from the image taking unit 1 is output to the controller 10. In step S4, the controller 10 computes a shift amount Xa1' based on the image of the eye obtained by the image pickup operation performed in the second state using formula (1) presented above.

In step S5, a determination is made as to whether or not the shift amount Xa1 in the first state and the shift amount Xa1' in the second state are different from each other. If it is determined that shift amount Xa1 and shift amount Xa1' are different from each other, the process proceeds to step S6. When shift amount Xa1 and shift amount Xa1' are different from each other, there should be a magnification error. On the other hand, if shift amount Xa1 and shift amount Xa1' are not different, this process is terminated.

Figure 6:
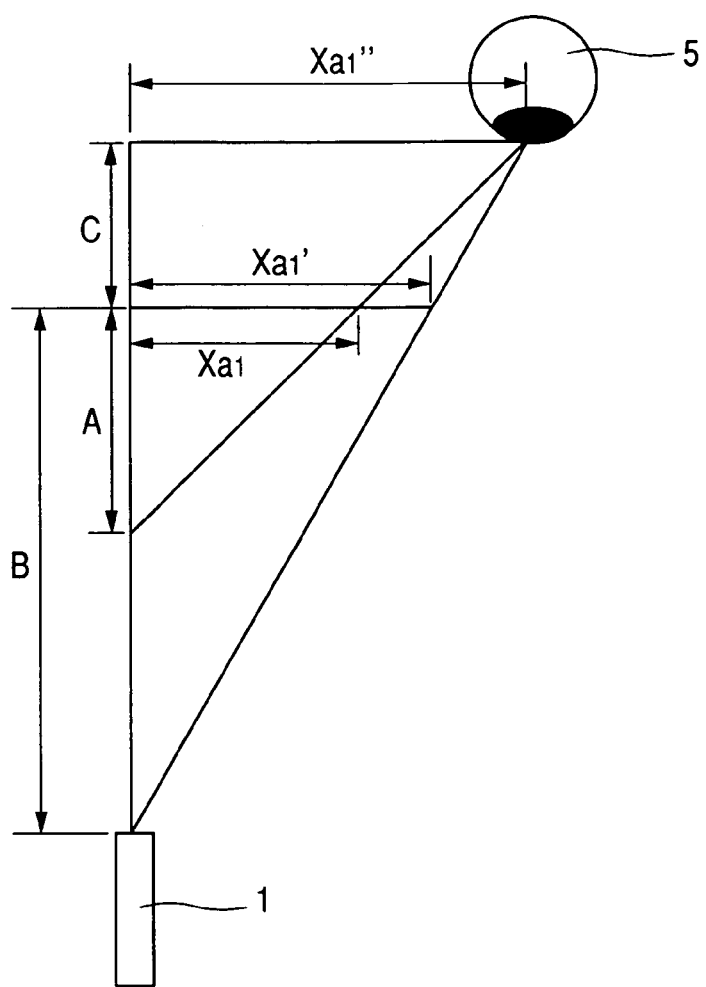
FIG. 6 is a diagram illustrating a shift amount of the pupil position in the first embodiment in a case where there is a magnification error.

Here, the positional relationship between the eye 5 and the image taking unit 1 in the state in which a magnification error is present will be described with reference to FIG. 6. In FIG. 6, the display optical system 4 is not illustrated.

In FIG. 6, sign A represents the distance between the image taking unit 1 and the eye 5 in the first state. In this state, the eye 5 is at the eye position corresponding to the designed value of the display optical system 4. In this embodiment, distance A is 20 mm, which is the aforementioned designed eye relief value.

Sign B represents the distance between the image taking unit 1 and the eye 5 in the second state. In this state, the eye 5 is at the eye position corresponding to the design vale of the display optical system 4. In this embodiment, the image taking unit 1 has been moved away from the eye 5 by 10 mm, and distance B is 30 mm.

Sign C represents the sift amount of the actual eye position at which the observer observes images from the eye position corresponding to the design value of the display optical system 4.

It is possible to compute a shift amount with magnification error correction, namely the shift amount Xa1″ of the pupil position in the actual observation state by substituting known values of A, B, Xa1' and Xa1 in formula (2) presented below. Thus, a correct pupil position can be detected.

$$X''_{a1} = \frac{(B-A)X_{a1}X'_{a1}}{BX_{a1} - AX'_{a1}} \quad (2)$$

Figure 5:
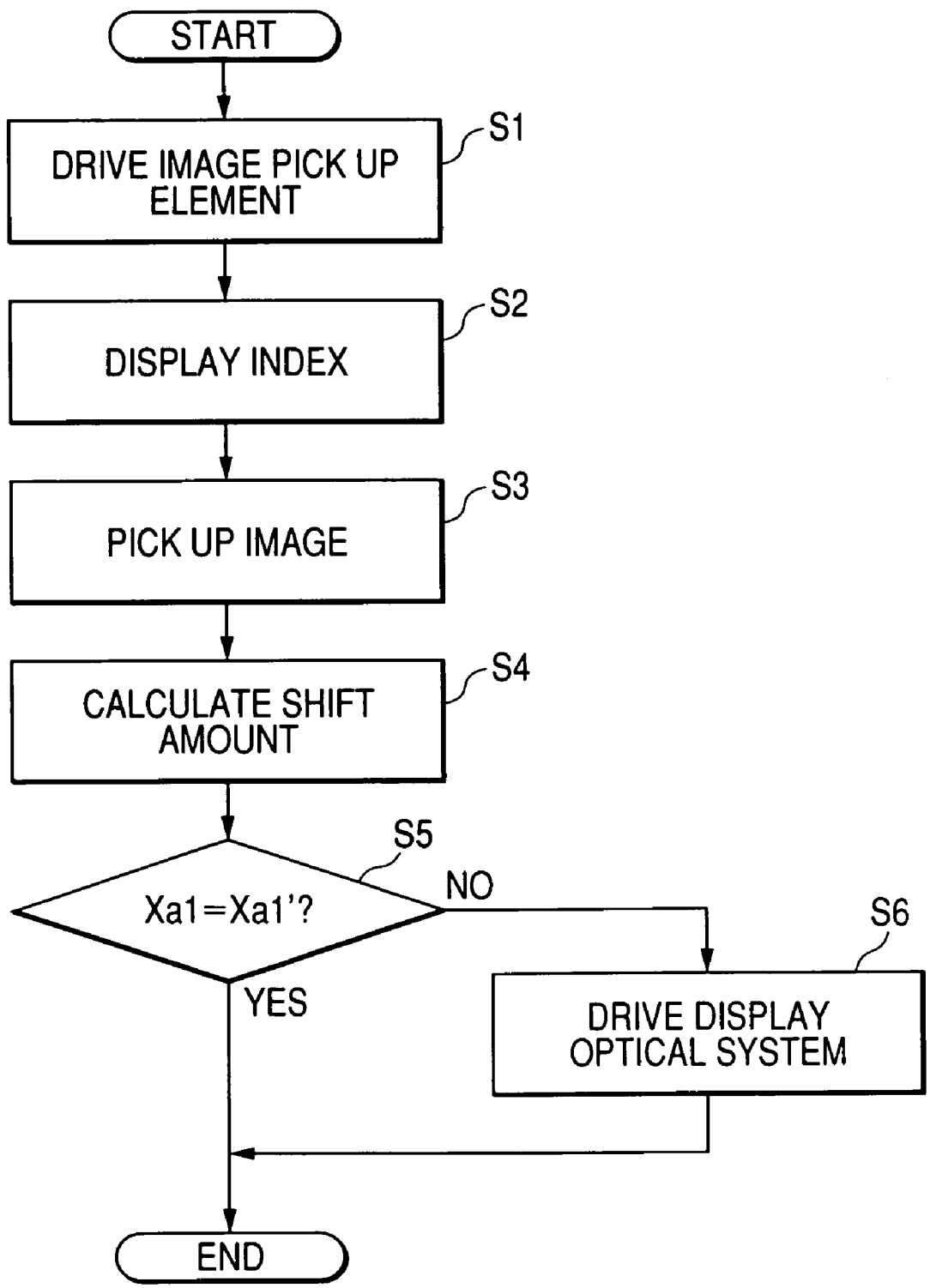
FIG. 5 is a flow chart of a process of driving a display optical system according to the first embodiment.

In the next step S6 in FIG. 5, the controller 10 controls driving of the second drive unit 12 based on the shift amount Xa1″ to move the display optical system 4 so that the position of the pupil of the observer coincides with the optical axis position of the display optical system 4. After that, the process is terminated.

As described above, when it is determined that a magnification error is present, the display optical system 4 is driven based on the actual shift amount Xa1″ of the pupil position to align the optical axis of the display optical system 4 and the pupil position substantially. Thus, the observer can observe displayed images on the image forming element 2 without eclipse.

Moreover, since the display optical system 4 is moved based on the correct pupil position thus detected, it is not necessary to make the diameter of the pupil of the display optical system 4 large. Accordingly, it is possible to prevent an increase in the size of the display optical system 4. In addition, it is possible to prevent an increase in the size of the HMD equipped with the display optical system 4 and an increase in the weight of the HMD.

To correct magnification errors, the HMD may have the structure described in the following. That is, the image taking unit 1 and the display optical system 4 may be constructed in such a way that they can move integrally so that the image taking unit 1 in the first state and the display optical system 4 may be moved in the horizontal direction by a predetermined amount, and an image pickup operation may be performed in the second state, that is, in the state realized after moving the image taking unit 1 and the display optical system 4.

Figure 7:
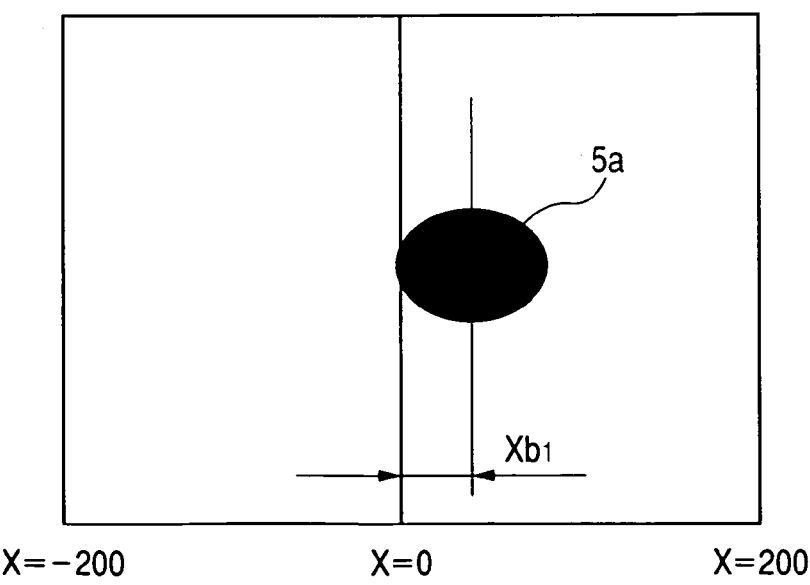
FIG. 7 is a diagram showing a shift amount after an image taking unit has been moved in the first embodiment.

Here, it is assumed, for example, that the image taking unit 1 and the display optical system 4 are moved in the horizontal direction by 3 mm from the first state shown in FIG. 4, to realize the second state. It is also assumed that the image of the eye obtained by an image pickup operation performed in the second state is like that shown in FIG. 7. Then, a shift amount Xb1 is obtained using formula (1) presented before.

In this case, if the difference between shift amount Xb1 and shift amount Xa1 is not equal to the movement amount 3 mm of the image taking unit 1 and the display optical system 4, it should be considered that a magnification error is present.

Figure 8:
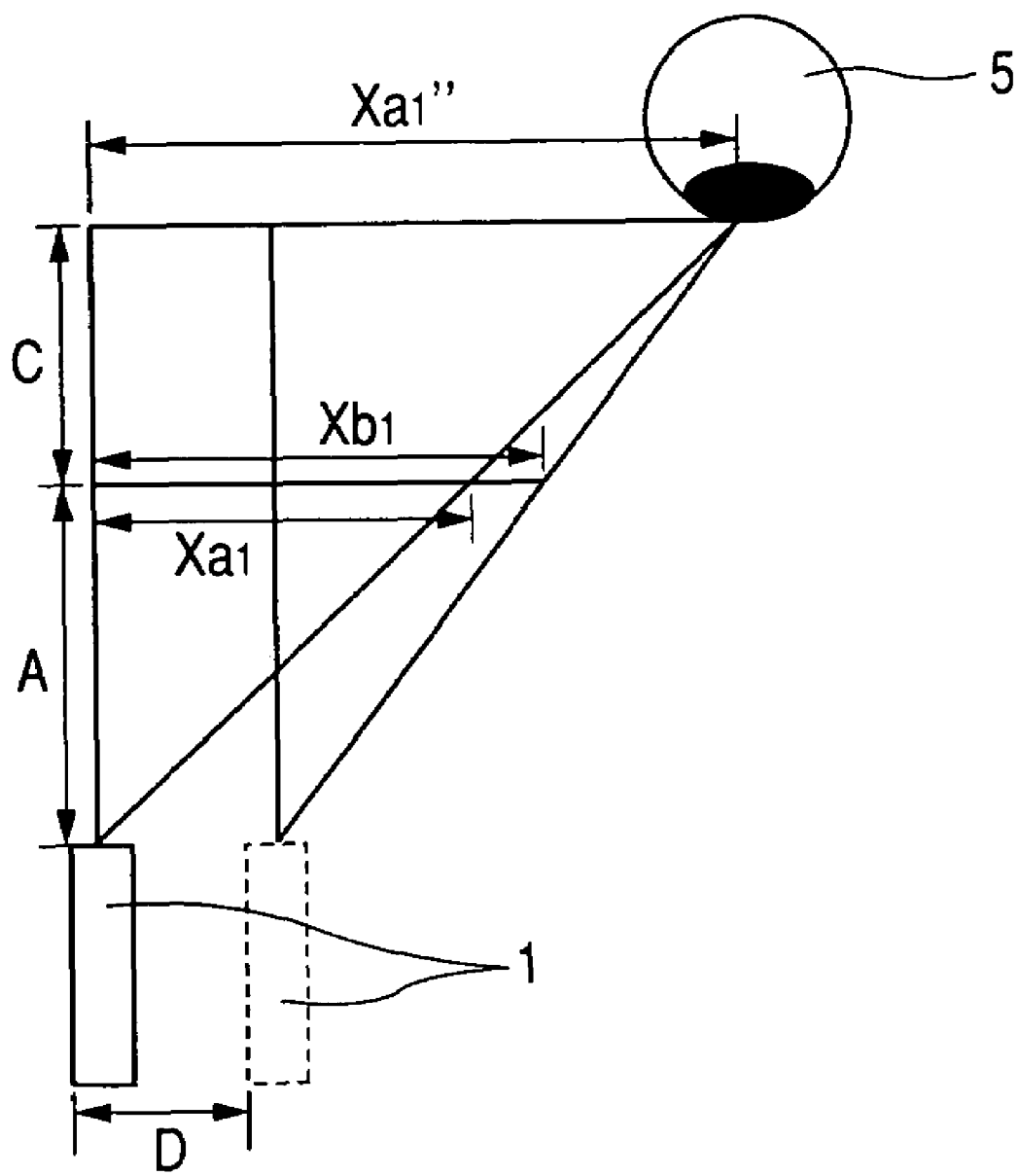
FIG. 8 is a diagram illustrating a shift amount of the pupil position in the first embodiment in a case where there is a magnification error.

The positional relationship between the image taking unit 1 and the eye 5 in the case where the image taking unit 1 and the display optical system 4 have been moved in the horizontal direction will be described with reference to FIG. 8. In FIG. 8, the display optical system 4 is not illustrated.

In FIG. 8, sign A represents the distance between the image taking unit 1 and the eye 5 in the first state. Here, the eye 5 is at the position corresponding to the designed value of the display optical system 4. In this embodiment, distance A is equal to 20 mm, which is the aforementioned designed value of the eye relief.

Sign C represents the sift amount of the actual eye position at which the observer observes images from the eye position corresponding to the design value of the display optical system 4. Sign D represents the distance over which the image taking unit 1 has moved, which is 3 mm in this case as described above.

It is possible to compute a shift amount with magnification error correction, namely the shift amount Xa1" of the pupil position in the actual observation state by substituting known values of A, C, D, Xa1 and Xb1 in formula (3) presented below.

$$X''_{a1} = \frac{DX_{a1}}{X_{a1} - X_{b1} + D} \quad (3)$$

The display optical system 4 is moved based on the shift amount Xa1" in such a way that the optical axis position of the display optical system 4 coincides with the pupil position. Thus, the observer can observe images displayed on the image forming element 2 without eclipse, as with the above-described case.

Although the foregoing description has been directed to the case where the shift amount of the pupil position in the horizontal direction is detected, it is also possible to detect the shift amount of the pupil position in the vertical direction (i.e. the up and down direction in FIG. 1A), namely the shift amount with respect to the up and down direction of the HMD, by using the detection method same as that of this embodiment.

Second Embodiment

Next, an HMD according to a second embodiment of the present invention will be described. The HMD of this embodiment is adapted to detect the direction of line of sight of the observer.

Figure 9A:
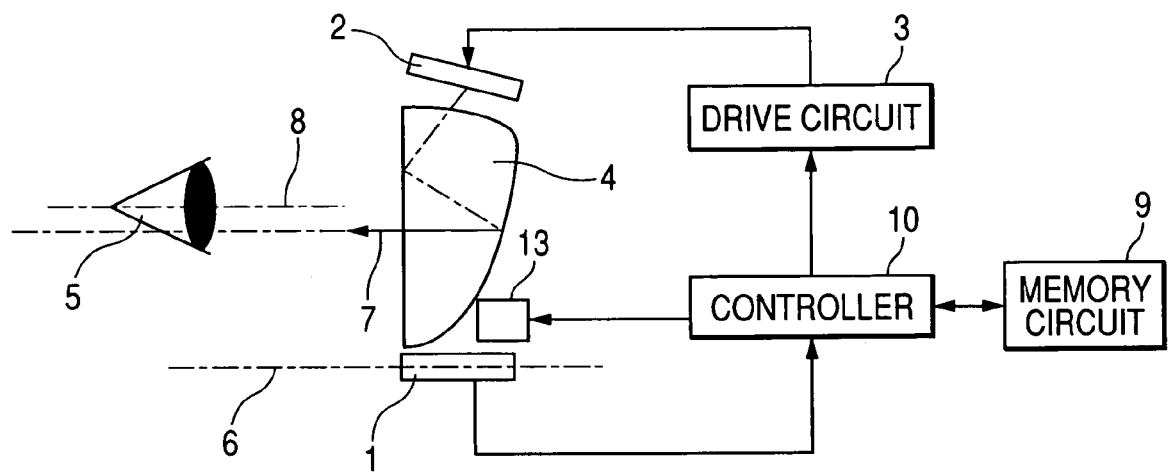
FIG. 9A is a side view schematically showing the structure of an HMD according to a second embodiment of the present invention.
Figure 9B:
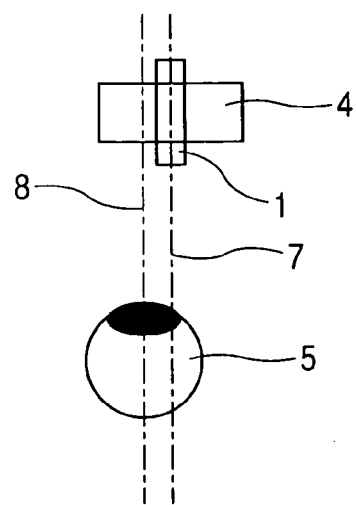
FIG. 9B is a top view thereof.

FIGS. 9A and 9B schematically show the basic structure of the HMD of this embodiment. FIG. 9A is a side view schematically showing the inner structure of the HMD according to this embodiment. FIG. 9B is a top view of the inner structure. In FIGS. 9A and 9B, the components same as those in the first embodiment are designated by the same reference signs and descriptions thereof will be omitted.

In this embodiment, the image taking unit 1 and the display optical system 4 are disposed in such a way that the optical axis 6 of the image taking unit 1 and the emerging optical axis 7 of the display optical system 4 are in the same plane and substantially parallel to each other in that plane.

The image taking unit 1 and the display optical system 4 are adapted to be moved integrally by a drive unit 13. The drive unit 13 drives them when it receives a command from a controller 10.

Reference numeral 9 designates a memory circuit, which stores a signal (index position information) output from the drive circuit 3 to the image display element 2 and image data picked up by the image taking unit 1, wherein the signal and the image data are associated with each other.

In this embodiment also, as with the first embodiment, the design value of the eye relief of the display optical system 4 is 20 mm, and the horizontal image pickup range at a distance of 20 mm from the display optical system 4 is set to 20 mm.

When an observer wears the HMD of this embodiment and depresses a measurement start button (not shown), an image of an eye of the observer is picked up by the image taking unit 1. When an image of the eye of the observer is to be picked up, it is necessary that the emerging optical axis 7 of the display optical system 4 and the line of sight 8 of the observer be substantially parallel to each other. In the case where the emerging optical axis 7 and the line of sight 8 are not substantially parallel, a displacement will remain even if the optical axis position of the display optical system 4 is aligned with the detected position of the pupil of the observer.

Figure 10:
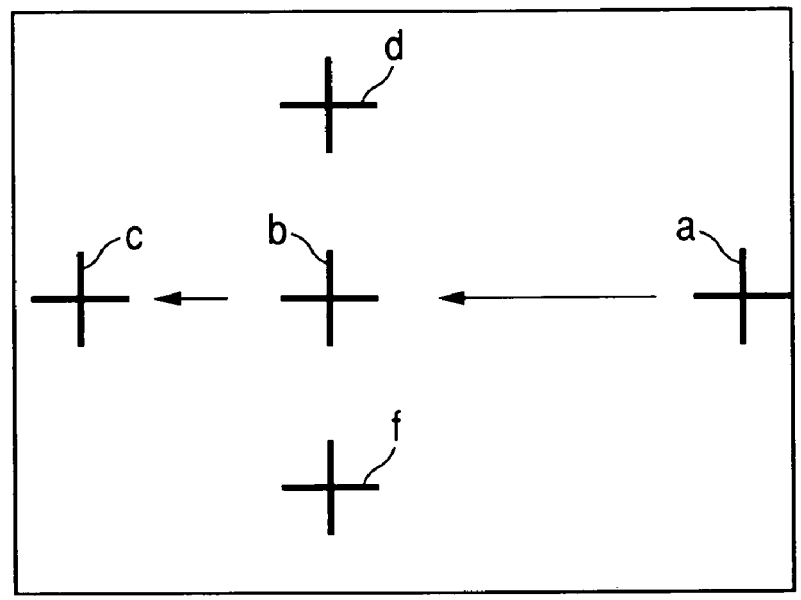
FIG. 10 illustrates how an index is displayed in the HMD according to the second embodiment.

When the measurement start button is depressed, a cross-shaped index is displayed at the right end a of the display screen of the image forming element 2 as shown in FIG. 10. The index is moved in the direction indicated by the arrows in FIG. 10 by small steps. For example, the index is displayed at display positions b and c. After the index has been moved to display position c, the index is displayed sequentially from the upper side (the upper side in FIG. 10) to the lower side of the display screen in the order of display position d display position b and display position f.

The index is displayed in the above-described way to instruct the observer to follow it with his/her eye. The index may be displayed as a motion picture. The index may be moved continuously from the right end to the left end or from the upper end to the lower end. The order and direction of display of the index may be modified fitly.

Figure 11:
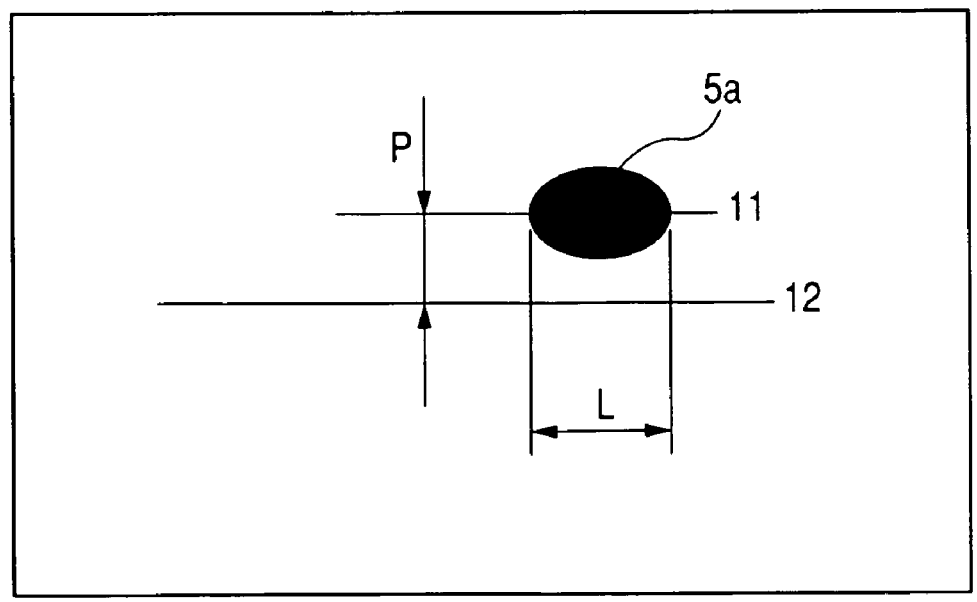
FIG. 11 shows a shift amount of the pupil position in the second embodiment.

Images of the eye are consecutively picked up (at every position of the index displayed) while the observer follows the displayed index with his/her eye. In addition, as shown in FIG. 11, the horizontal width L of the colored part 5a of the eye in the image and the distance (shift amount) P between the horizontal line 11 passing through the center of the pupil and the center line 12 of the image in each of the plurality of images obtained by consecutive image pickup operations are associated with each other and stored in the memory circuit 9.

Figure 12A:
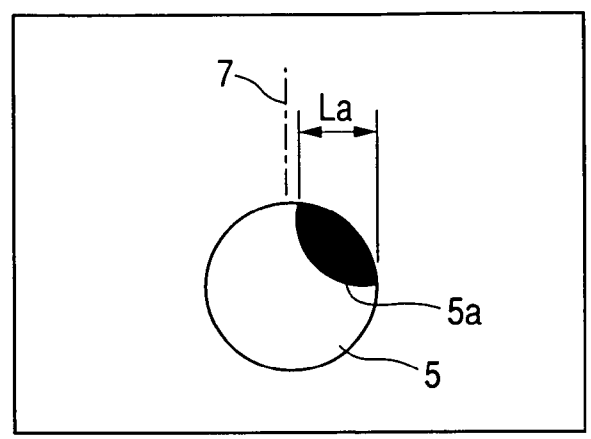
FIGS. 12A, 12B and 12C illustrate observing states of an eye in the second embodiment.
Figure 12B:
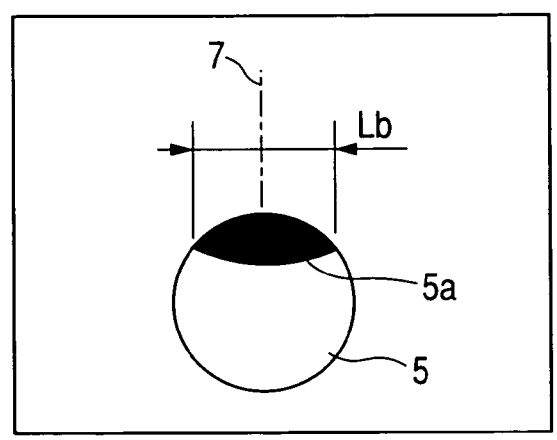
Figure 12C:
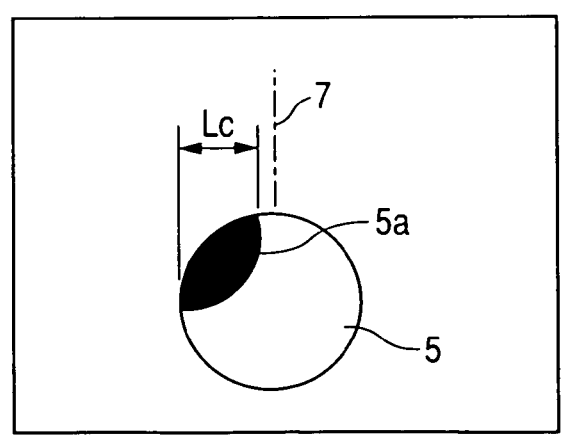

FIGS. 12A to 12C show states of the eye 5 while following the index.

In the state in which the eye 5 of the observer is tilted to one of the left and right directions (horizontal directions), in other words, in the state in which the line of sight 8 of the observer is not substantially parallel to the emerging optical axis 7 of the display optical system 4 but inclined to it, the horizontal length (or width) (in the direction orthogonal to the emerging optical axis 7) of the colored part 5a of the eye 5 is La shown in FIG. 12A.

On the other hand, in the state in which the line of sight 8 of the observer is substantially parallel to the emerging optical axis 7 of the display optical system 4, the horizontal length (or width) of the colored part 5a of the eye 5 is Lb shown in FIG. 12B.

In the state in which the eye 5 is tilted to the other direction, where the line of sight 8 of the observer is not substantially parallel to the emerging optical axis 7 of the display optical system 4 but inclined to it, the horizontal length (or width) of the colored part 5a of the eye 5 is Lc shown in FIG. 12C.

In the states shown in FIGS. 12A and 12C, the line of sight 8 is inclined to the emerging optical axis 7, and therefore lengths La and Lc are shorter than length Lb, namely, length Lb in the state shown in FIG. 12B is the largest.

In this embodiment, the state of the eye 5 shown in FIG. 12B, or the state in which the width of the colored part 5a of the eye 5 becomes the largest, is determined based on multiple image data obtained by successive image pickup operations performed by the image taking unit 1. Then, the index at the position associated with the state shown in FIG. 12B is displayed on the image forming element 2 again. The observer is instructed to see the displayed index again, and an image of the eye 5 while observing is picked up. This state will be referred to as the first state.

Based on the image data obtained by the image pickup operation performed in the first state, both ends of the colored part 5a of the eye are extracted, and the center of them is set as the pupil position.

With respect to the vertical direction, it is often the case that the upper and lower portions of the colored part 5a are covered by the eyelid. Therefore, the portion covered by the eyelid is supplemented (or extrapolated) based on the radius of curvature of the curve of the colored part 5a obtained by the image pickup operation, and the detection process same as the above-described process for the horizontal direction is performed.

Individual variations in the shift amount among observers who wear the HMD are larger in the vertical direction than in the horizontal direction. In this embodiment, it is assumed that the HMD that the observer wears is at a position near the position suitable for observation, and the vertical shift amount of the pupil position is detected based on the shift amount P shown in FIG. 11 to correct a small displacement.

In this embodiment, it is assumed that the horizontal resolution of the image taking unit 1 is 400. The point of origin (the reference position) is set at the center of the image obtained by the image pickup operation, and the X coordinate is set in the range of ±200 and the Y coordinate is set in the range of ±200 as shown in FIG. 11.

Figure 13:
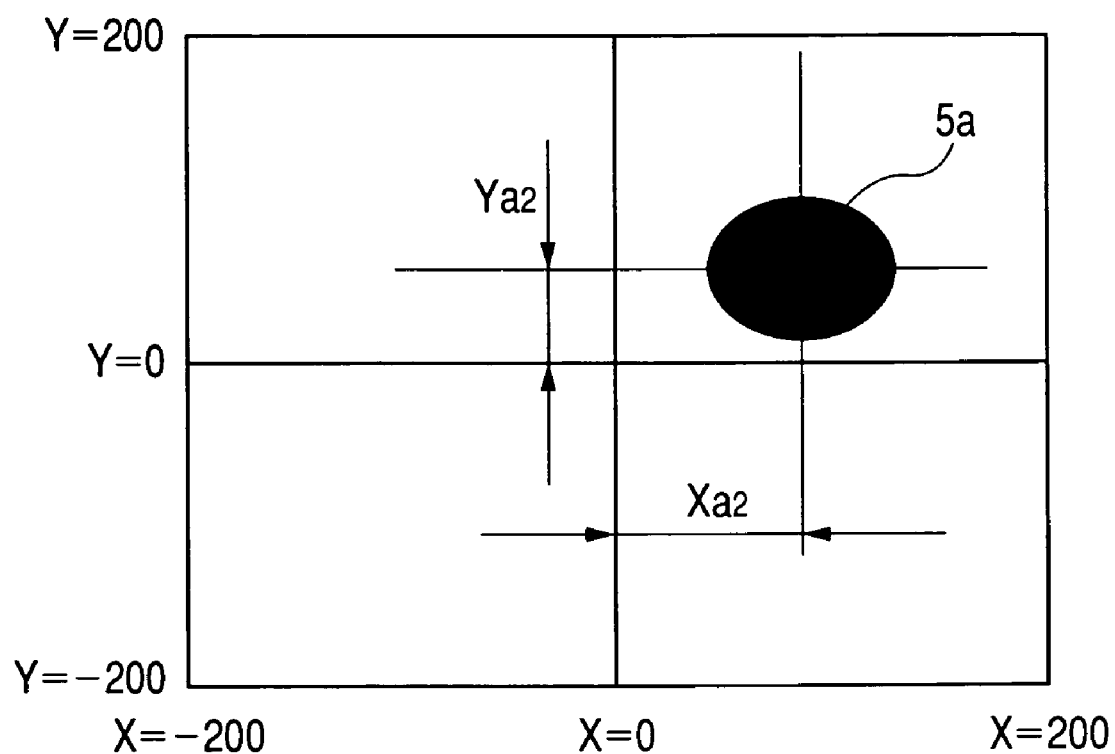
FIG. 13 is a diagram showing a shift amount of the pupil position in the second embodiment.

By using formula (1) presented in the description of the first embodiment, it is possible to determine the shift amount Xa2 in the X direction (or the horizontal direction) and the shift amount Ya2 in the Y direction (or the vertical direction) as shown in FIG. 13. Shift amount Xa2 is the shift amount (or deviation) of the pupil position in the X direction from the center of the image (X=0), and shift amount Ya2 is the shift amount of the pupil position in the Y direction from the center of the image (Y=0).

The image of the eye obtained by the image pickup operation is an image under the state in which the eye 5 of the observer is at the position corresponding to the design value 20 mm of the eye relief. However, the eye of the observer is sometimes not at the desired eye relief position when he/she observes the display optical system 4. In such cases, the picked up image of the eye includes a magnification error, and the pupil position at that time may be displaced from the pupil position with the prescribed eye relief.

Therefore, it is necessary to correct the above-mentioned displacement (or the magnification error). The method of correcting the magnification error may be that described in the description of the first embodiment.

In this embodiment, the image taking unit 1 is moved away from the eye 5 by, for example, 10 mm so that the image pickup range at a distance of 30 mm from the display optical system 4 becomes 40 mm. Then, the index is displayed at the position same as that in the first state on the image forming element 2 to instruct the observer to see the index. This state will be referred to as the second state.

Then, an image pickup operation is performed in the second state. A shift amount Xa2' is determined based on the image of the eye obtained by the image pickup operation performed in the second state using formula (1) presented in the description of the first embodiment. If the shift amount Xa2 in the first state and the shift amount in the second state Xa2' are different from each other, there should be a magnification error.

If these shift amounts are different, a shift amount with magnification error correction, namely a shift amount Xa2" of the pupil position in the actual observation state is determined using formula (2) presented in the description of the first embodiment.

On the other hand, when there is a magnification error in the X direction, there also is a magnification error in the Y direction. Therefore, a shift amount with magnification correction in the Y direction, namely a shift amount Ya2" in the Y direction of the pupil position in the actual observation state is obtained using formulas (1) and (2).

The controller 10 controls driving of the drive unit 13 based on the shift amounts Xa2", Ya2" thus determined to move the display optical system 4 (together with the image taking unit 1) in the X and Y directions so that the position of the pupil of the observer coincides with the optical axis position of the display optical system 4. Thus, the observer can observe images displayed on the image forming element 2 without eclipse. Since the display optical system 4 is moved, it is not necessary to increase the size of the entire display optical system 4 in order to enlarge the pupil diameter.

On the other hand, in this embodiment, images of the eye picked up while the observer is gazing at and following the index in the observer's pupil position detection process and index position information are associated with each other and stored in the memory circuit 9.

Since this data is one for the initial state (the first state) of the display optical system 4, correction is made on the data based on the movement amounts of the display optical system 4 in the X and Y directions in order that the pupil position and the optical axis position of the display optical system are substantially aligned with each other.

After the pupil position and the optical axis position of the display optical system 4 have been substantially aligned with each other, image pickup of the eye of the observer is consecutively performed, and the width L of the colored part 5a and shift amount P shown in FIG. 11 are detected. The controller (line of sight detection portion) 10 can detect which position in the display area of the image forming element 2 the observer is gazing at by comparing the data obtained by the detection and the above-described corrected data.

The image pickup of the eye is performed every time the observer wears the HMD, and the data in the memory circuit 9 is updated. Thus, it is possible to detect the point-of-gaze and the direction of the line of sight irrespective of individual variations such as variations in the size of the eyeball.

Then, the display optical system 4 is moved in such a way that the point-of-gaze or the direction of the line of sight thus detected is substantially aligned with the optical axis of the display optical system 4. Thus, the observer can observe images displayed on the image forming element 2 without eclipse.

Third Embodiment

Next, an HMD according to the third embodiment of the present invention will be described. In the HMD of this embodiment, an image display element and a display optical system etc. are provided for each of both eyes of the observer, and the interpupillary distance of the observer can be detected.

Figure 14A:
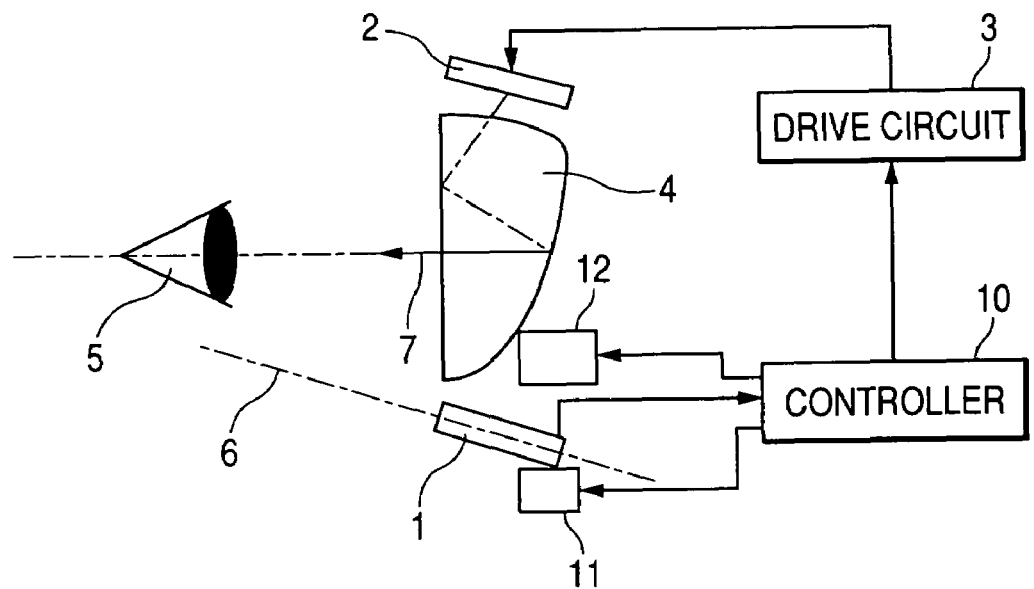
FIG. 14A is a side view schematically showing the structure of an HMD according to a third embodiment of the present invention.
Figure 14B:
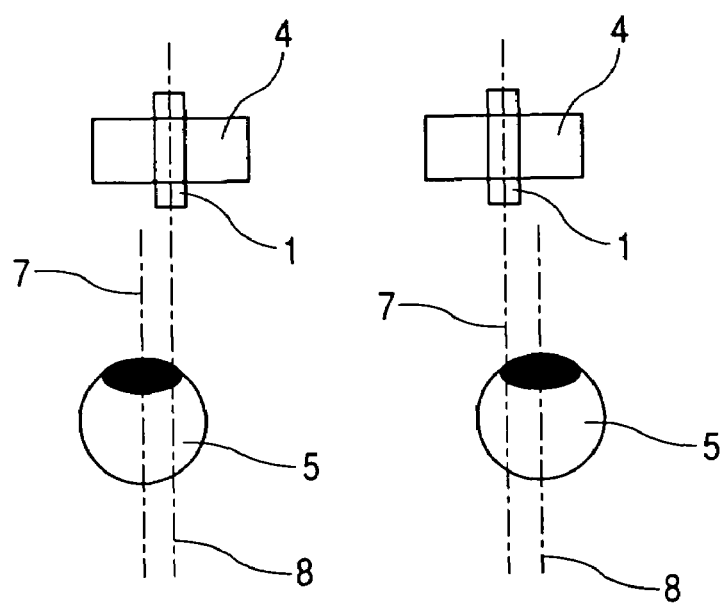
FIG. 14B is a top view thereof.

FIG. 14A is a side view schematically showing the inner structure of the HMD according to this embodiment. FIG. 14B is a top view of the inner structure. In FIGS. 14A and 14B, the members same as those in the first and second embodiments are designated by the same reference signs and descriptions thereof will be omitted.

The image taking unit 1 and the display optical system 4 are disposed in such a way that the optical axis 6 of the image taking unit 1 and the emerging optical axis 7 of the display optical system 4 are in the same plane. In addition, the image taking unit 1 and the display optical system 4 may be disposed in such a way that the optical axis 6 and the emerging optical axis 7 are substantially parallel in the above-mentioned plane.

In this embodiment, image forming elements 2 for right and left eyes are driven by a single drive circuit 3. However, a drive circuit may be provided for each of the image forming elements.

It is generally said that the interpupillary distance of human eyes are in the range of approximately 55 mm to 75 mm, and the most common interpupillary distance is approximately 65 mm. The typical diameter of the colored part of eyes is approximately 10 mm.

Therefore, by assuming that the interpupillary distance is 65 mm, setting a design value of the eye relief of the display optical system 4 to 20 mm, and setting the horizontal image pickup range at a distance of 20 mm from the display optical system 4 to 30 mm when each image taking unit 1 is disposed on the center axis, with respect to the horizontal direction, of the corresponding display optical system 4, it is possible to pick up an image of the whole eye even if the position of pupils of the observer who wears the HMD are displaced from the design value by ±10 mm in the horizontal direction.

In the HMD of this embodiment, when the observer wears the HMD and depresses a measurement start button (not shown) provided on the HMD, the eyes 5 of the observer are irradiated with illumination light. Light reflected from the eyes 5 enters the image taking units 1, and image taking operation is performed by the image taking units 1.

Since irradiation of the eyes 5 of the observer with visible illumination light is sometimes annoying to the observer, infrared light outside the visible region is used as illumination light in this embodiment.

When the pupil position is detected, the left and right eyes are converging unless the eyes are focused at infinity. Accordingly, the value of the interpupillary distance computed based on the distance between the pupil positions of the left and right eyes contains an error. Even when the optical axis position of the display optical system 4 is aligned with the detected pupil position, there is a possibility that there is a misalignment between the emerging optical axis 7 of the display optical system 4 and the line of sight 8 of the observer, as will be described later.

Figure 15:
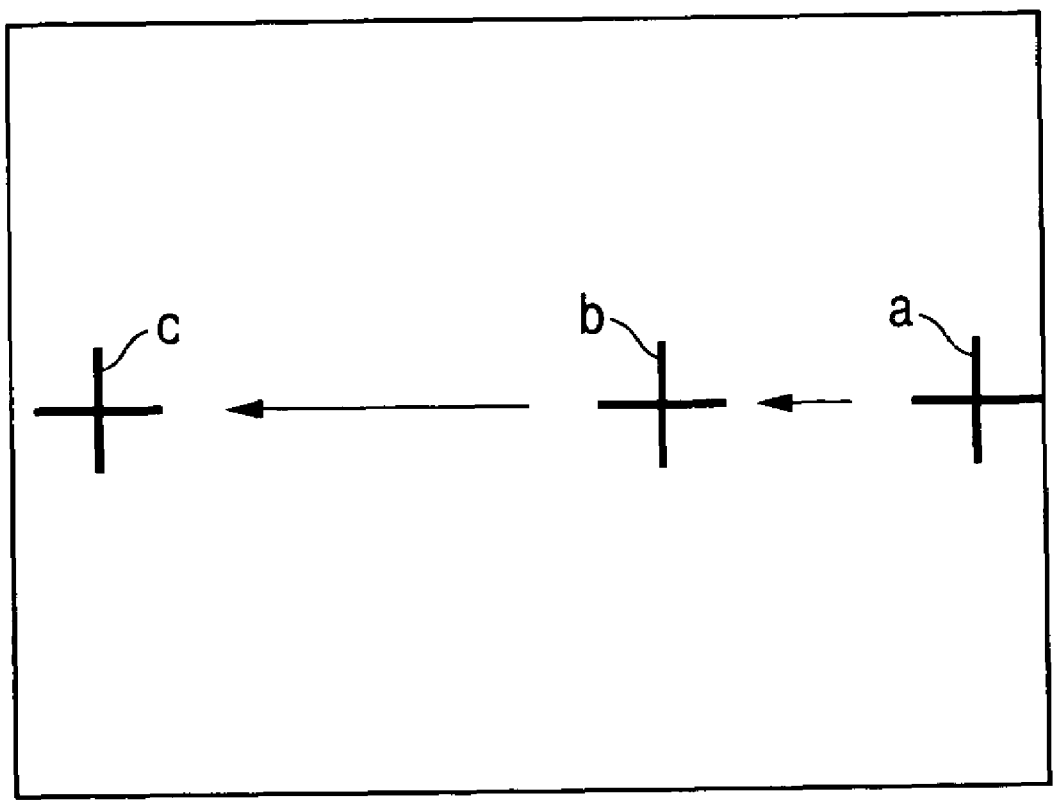
FIG. 15 illustrates how an index is displayed in the HMD according to the third embodiment.

In the HMD of this embodiment, when the observer depresses the measurement start button, a cross shaped index is displayed at the right end a of the display area of each of the image forming elements 2 for the left and right eyes as shown in FIG. 15. The index is moved in the direction indicated by the arrows in FIG. 15 by small steps and displayed at position b and position c in the mentioned order. Thus, the observer is instructed to follow the index with his/her eyes.

The index may be continuously moved by displaying it as a motion picture. The direction of movement of the index may be modified fitly.

In this embodiment, images of the eyes are consecutively picked up (at every position of the index displayed) while the index is moved.

Figure 16A:
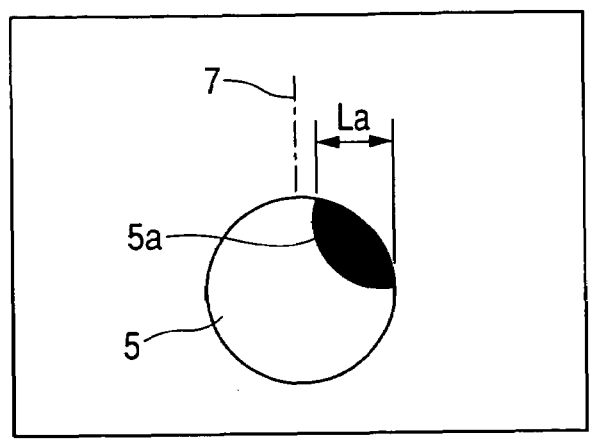
FIGS. 16A, 16B and 16C illustrate observing states of an eye in the third embodiment.
Figure 16B:
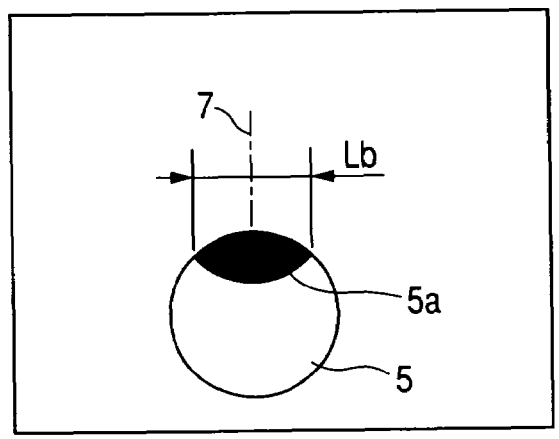
Figure 16C:
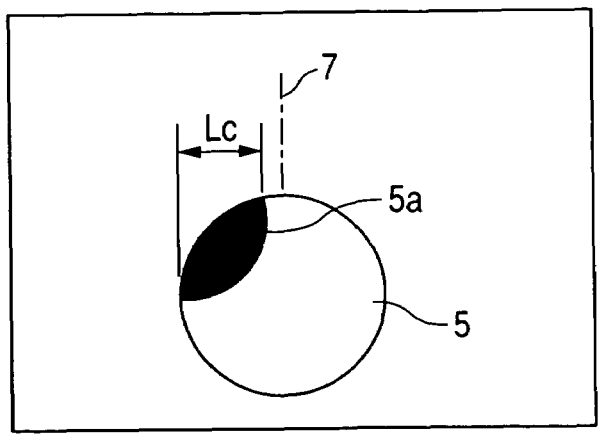

FIGS. 16A to 16C show states of the right eye 5 while following the index.

In the state in which the eye 5 of the observer is not seeing infinity but tilted to one of the left and right directions, in other words, in the state in which the line of sight 8 of the observer is not substantially parallel to the emerging optical axis 7 of the display optical system 4 but inclined to it, the horizontal length (or width) (in the direction orthogonal to the emerging optical axis 7) of the colored part 5a of the eye 5 is La shown in FIG. 16A.

On the other hand, in the case where the observer is seeing infinity and the line of sight 8 of the observer is substantially parallel to the emerging optical axis 7 of the display optical system 4, the horizontal length (or width) of the colored part 5a of the eye 5 is Lb shown in FIG. 16B.

In the state in which the eye 5 is tilted to the other direction, where the line of sight 8 of the observer is not substantially parallel to the emerging optical axis 7 of the display optical system 4 but inclined to it, the horizontal length (or width) of the colored part 5a of the eye 5 is Lc shown in FIG. 16C.

In the states shown in FIGS. 16A and 16C, the line of sight 8 is inclined to the emerging optical axis 7, and therefore lengths La and Lc are shorter than length Lb, namely, length Lb in the state shown in FIG. 16B is the largest.

in this embodiment, the state of the eye 5 shown in FIG. 16B, or the state in which the width of the colored part 5a of the eye 5 becomes the largest, is determined based on multiple image data obtained by successive image pickup operations performed by the image taking unit 1. Then, the index at the position associated with the state shown in FIG. 16B is displayed on the image forming element 2 again. The observer is instructed to see the displayed index again, and an image of the eye 5 while observing is picked up. This state will be referred to as the first state.

Based on the image data (an image of the eye) obtained by the image pickup operation performed in the first state, both ends of the colored part 5a of the eye are extracted, and the center of them is set as the pupil position.

Here, the resolution in detecting the pupil position depends on the resolution of the image taking unit 1. For example if the pupil position is to be detected with 0.1 mm pitch, the horizontal resolution of the image taking unit 1 should be 300 (pixels) or more, since the image pickup range in the horizontal direction is set to 30 mm as described before.

Figure 17:
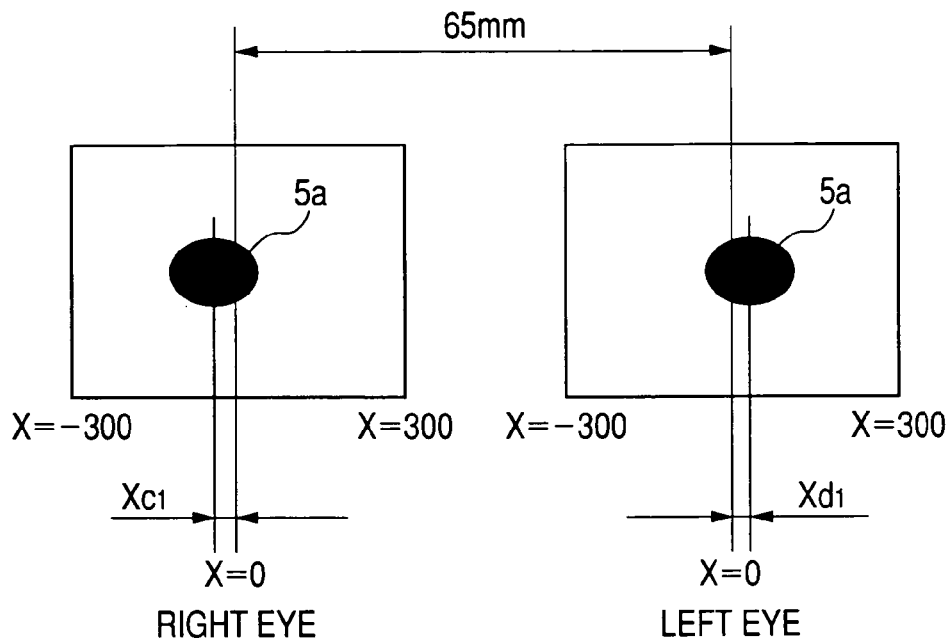
FIG. 17 is a diagram showing a shift amount of the pupil position in the third embodiment.

In this embodiment, it is assumed that the horizontal resolution of the image taking unit 1 is 600. The point of origin is set at the center of the image obtained by the image pickup operation, and the X coordinate is set in the range of ±300 as shown in FIG. 17. In addition, the shift amount in the X direction (horizontal direction) of the pupil position of the right eye from the point of origin is represented by Xc1. The shift amount in the X direction of the pupil position of the left eye from the point of origin is represented by Xd1.

Shift amounts Xc1 and Xd1 can be obtained from formula (1) presented in the description of the first embodiment.

The image of the eye obtained by the image pickup operation is an image under the state in which the eye 5 of the observer is at the position corresponding to the design value 20 mm of the eye relief. However, the eye of the observer is sometimes not at the desired eye relief position when he/she observes the display optical system 4. In such cases, the picked up image of the eye includes a magnification error, and the pupil position at that time may be displaced from the pupil position with the prescribed eye relief.

Therefore, it is necessary to correct the above-mentioned error (i.e. the magnification error). One method of correcting the magnification error is to move the image taking unit 1 in such a way that the distance between the eye 5 and the image taking unit 1 becomes larger than that before moving the image taking unit 1, in other words, to increase the optical path length as compared to that before moving the image taking unit 1 to enlarge the image pickup area. In the case where it is not possible to move the image taking unit 1 physically, the image pickup magnification may be changed to realize an optical effect equivalent to that realized by moving the image taking unit 1.

In this embodiment, the image taking unit 1 is moved away from the eye 5 by, for example, 10 mm so that the image pickup range at a distance of 30 mm from the display optical system 4 becomes 40 mm. Then, the index is displayed at the position same as that in the first state on the image forming element 2 to instruct the observer to see the index. This state will be referred to as the second state.

Then, an image pickup operation is performed in the second state. Shift amounts Xc1' and Xd1' are determined based on the images of the left and right eyes obtained by the image pickup operation performed in the second state using formula (1) presented in the description of the first embodiment. If the shift amounts Xc1 and Xd1 in the first state and the shift amounts in the second state Xc1' and Xd1' are different from each other, there should be a magnification error.

If there is a magnification error, shift amounts Xc1" and Xd1" in the actual observation state are determined using formula (2) presented in the description of the first embodiment, namely shift amounts with magnification error correction are determined.

To correct magnification errors, the HMD may have the structure described in the following. That is, as with the second embodiment, the image taking unit 1 and the display optical system 4 may be constructed in such a way that they can move integrally so that the image taking unit 1 in the first state and the display optical system 4 may be moved in the horizontal direction by a predetermined amount, and an image pickup operation may be performed in the second state, that is, the state realized after moving the image taking unit 1 and the display optical system 4.

Figure 18:
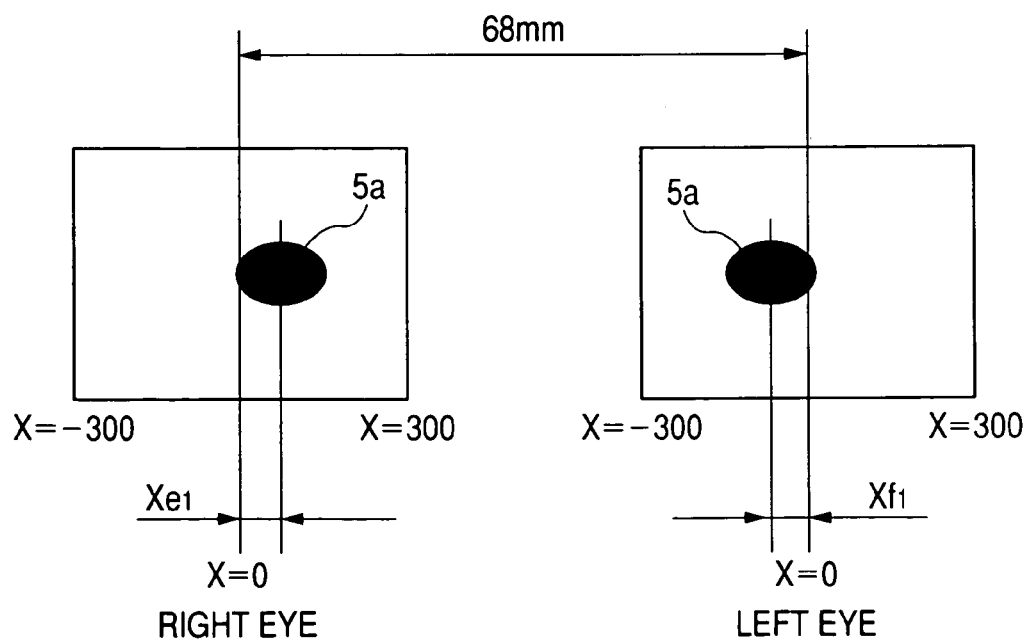
FIG. 18 is a diagram showing a shift amount of the pupil position in the third embodiment.

For example, each of the display optical systems 4 for the right eye and the display optical system 4 for the left eye in the state shown in FIG. 17 is moved outwardly by 1.5 mm to change the interpupillary distance to 68 mm. It is assumed that an image of the eyes picked up after the above change in the distance is like that shown in FIG. 18. If the difference between shift amount Xe1 and shift amount Xc1 computed using formula (1) presented in the description of the first embodiment is not 1.5 mm, or if the difference between shift amount Xf1 and shift amount Xd1 is not 1.5 mm, there should be a magnification error.

In cases where there is a magnification error, the controller 10 (interpupillary distance detection unit) 10 can compute a shift amount with magnification error correction, namely the shift amount of the pupil position in the actual observation state by using formula (3) presented in the description of the first embodiment. Thus, it is possible to detect correct pupil positions (the interpupillary distance).

In the first state, the measurement is performed in the state in which the center to center distance between the display optical system 4 for the left eye and the display optical system 4 for the right eye is set to 65 mm. Accordingly, it is possible to compute the interpupillary distance of the observer from shift amounts Xc1" and Xd1". In the second state after the display optical systems 4 have been moved, the center to center distance of the display optical systems 4 is 68 mm, and it is possible to determine the interpupillary distance by computing shift amounts Xe1" and Xf1" using formula (3) presented in the description of the first embodiment.

By correcting a magnification error, it is possible to detect a correct shift amount of the emerging optical axis 7 of the display optical system 4 relative to the position of the pupil of the observer for each of the left and right eyes. Each display optical system 4 (or the display optical system and the image taking unit) is moved based on the detected shift amount in such a way that the optical axis position of the display optical system 4 coincides with the pupil position. Thus, the observer can observe images displayed on the image forming element 2 without eclipse.

Fourth Embodiment

Next, an HMD according to the fourth embodiment of the present invention will be described. In the HMD of this embodiment, an image display element and a display optical system etc. are provided for each of both eyes of the observer, and the direction toward the gazing point (or the direction of the line of sight) of the observer can be detected.

Figure 19A:
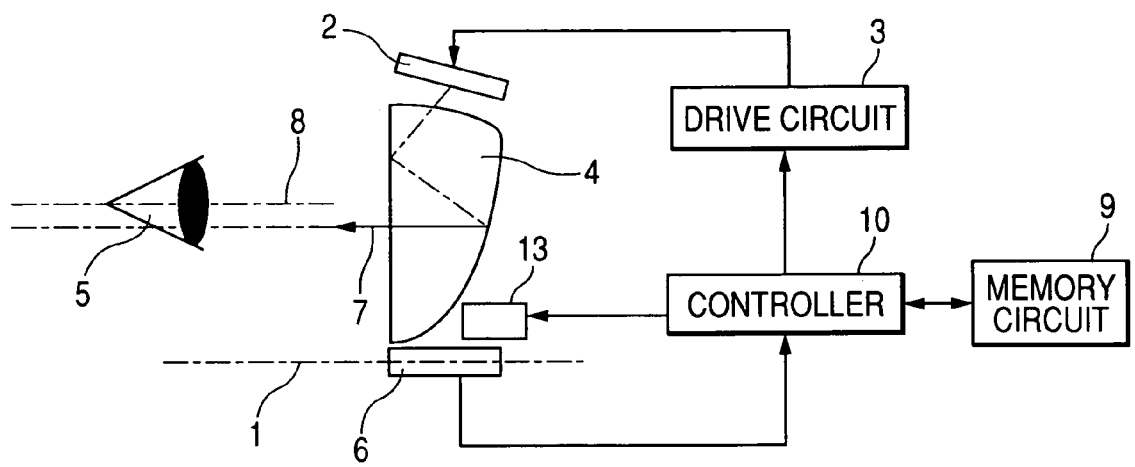
FIG. 19A is a side view schematically showing the structure of an HMD according to a fourth embodiment of the present invention.
Figure 19B:
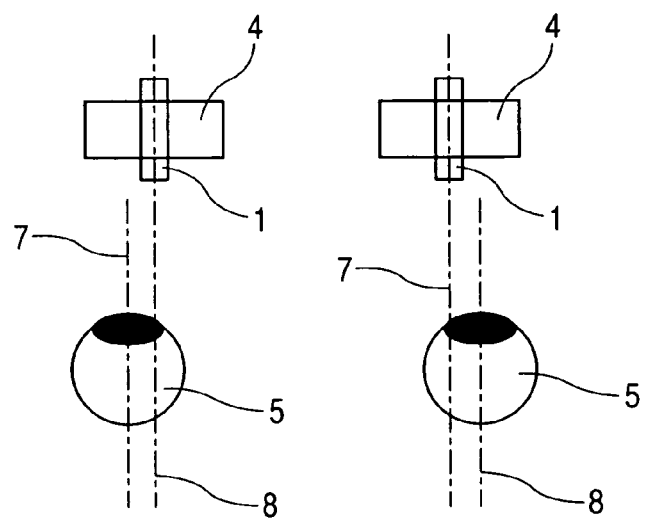
FIG. 19B is a top view thereof.

FIG. 19A is a side view schematically showing the inner structure of the HMD according to this embodiment. FIG. 19B is a top view of the inner structure. In FIGS. 19A and 19B, the members same as those in the first and second embodiments are designated by the same reference signs and descriptions thereof will be omitted.

The image taking unit 1 and the display optical system 4 are disposed in such a way that the optical axis 6 of the image taking unit 1 and the emerging optical axis 7 of the display optical system 4 are in the same plane and that the optical axis 6 and the emerging optical axis 7 are substantially parallel in that plane. The image taking unit 1 and the display optical system 4 can be moved integrally by a drive unit 13.

In this embodiment, a signal (information on the position of the index) output from the drive circuit 3 to the image forming element 2 and image data picked up by the image taking unit 1 are associated with each other and stored in the memory circuit 9.

Here, the interpupillary distance of the left and right eyes is assumed to be 65 mm, the design value of the eye relief of the display optical system 3 is set to 20 mm, and if each image taking unit 1 is disposed on the center axis with respect to the horizontal direction of the corresponding display optical system 4 the horizontal image pickup range at a distance of 20 mm from the display optical system 3 is set to 30 mm.

In this embodiment, the image forming elements 2 corresponding to the left and right eyes are driven by a single drive circuit 3. In addition, a single memory circuit 9 is provided. The drive circuit 3 and the memory circuit 9 may be provided for each of the image forming elements.

When the pupil position is detected, the left and right eyes are converging unless the eyes are focused at infinity. Accordingly, the value of the interpupillary distance of the observer computed based on the distance between the pupil positions of the left and right eyes contains an error. Even when the optical axis position of the display optical system 4 is aligned with the detected pupil position of the observer, there is a possibility that there is a misalignment between the emerging optical axis 7 of the display optical system 4 and the line of sight 8 of the observer, as will be described later.

Figure 20:
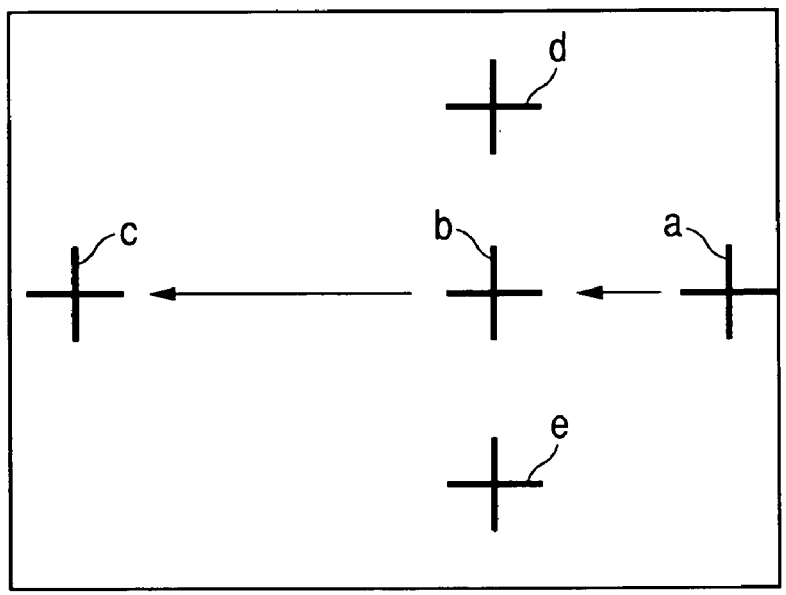
FIG. 20 illustrates how an index is displayed in the HMD according to the fourth embodiment.

When the observer wears the HMD of this embodiment and depresses the measurement start button (not shown), a cross shaped index is displayed at the right end a of the display area of each of the image forming elements 2 for the left and right eyes as shown in FIG. 20. The index is moved in the direction indicated by the arrows in FIG. 20 by small steps and displayed at position b and position c in the mentioned order. After the index is moved to display position c, it is displayed at display positions d, b and f in the mentioned order.

Thus, the index is moved to instruct the observer to follow the index with his/her eyes. The index may be continuously moved by displaying it as a motion picture. The direction of movement of the index may be modified fitly.

Images of the eyes are consecutively picked up (at every position of the index displayed) while the observer follows the displayed index with the eye. In addition, the horizontal width L of the colored part of the eye in the image and the distance (shift amount) P between the horizontal line 11 passing through the center of the pupil and the center line 12 of the image (see FIG. 21) in each of the plurality of images of the eye obtained by consecutive image pickup operations are associated with each other and stored in the memory circuit 9.

Figure 22A:
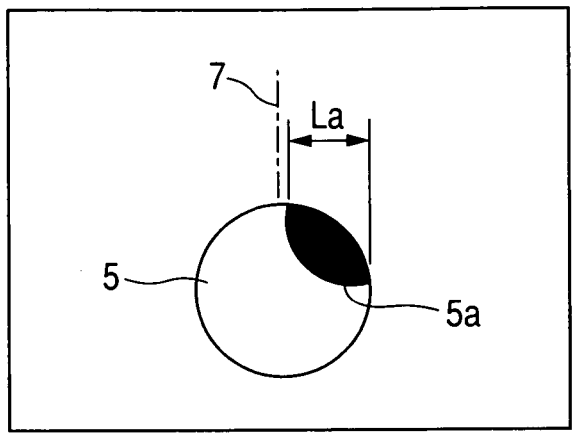
FIGS. 22A, 22B and 22C illustrate observing states of an eye in the fourth embodiment.
Figure 22B:
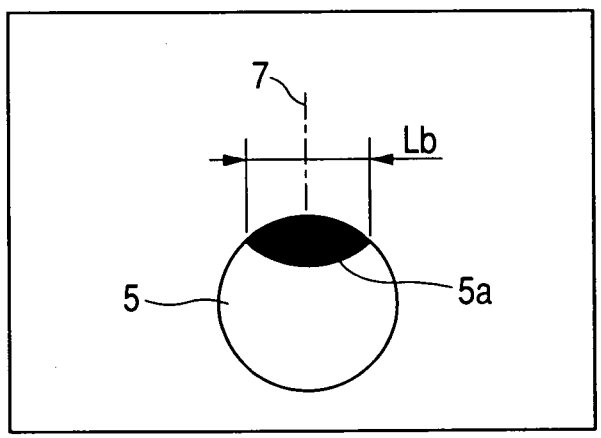
Figure 22C:
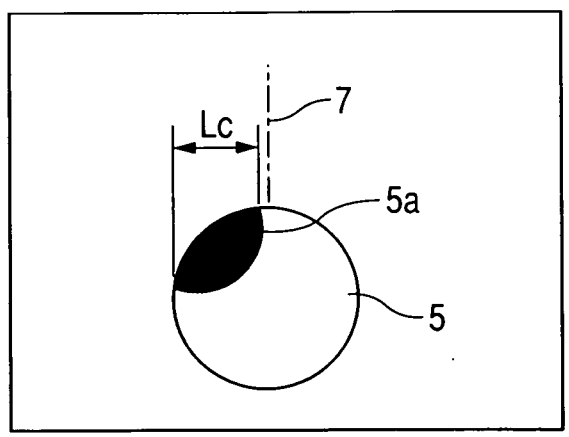

FIGS. 22A to 22C show states of the right eye 5 while following the index.

In the state in which the eye 5 of the observer is not seeing infinity but tilted to one of the left and right directions, in other words, in the state in which the line of sight 8 of the observer is not substantially parallel to the emerging optical axis 7 of the display optical system 4 but inclined to it, the horizontal length (or width) (in the direction orthogonal to the emerging optical axis 7) of the colored part of the eye 5 is La shown in FIG. 22A.

On the other hand, in the case where the observer is seeing infinity and the line of sight 8 of the observer is substantially parallel to the emerging optical axis 7 of the display optical system 4, the horizontal length (or width) of the colored part of the eye 5 is Lb shown in FIG. 22B.

In the state in which the eye 5 is tilted to the other direction, where the line of sight 8 of the observer is not substantially parallel to the emerging optical axis 7 of the display optical system 4 but inclined to it, the horizontal length (or width) of the colored part of the eye 5 is Lc shown in FIG. 22C.

In the states shown in FIGS. 22A and 22C, the line of sight 8 is inclined to the emerging optical axis 7, and therefore lengths La and Lc are shorter than length Lb, namely, length Lb in the state shown in FIG. 22B is the largest.

In this embodiment, the state of the eye 5 shown in FIG. 22B, or the state in which the width of the colored part 5a of the eye 5 becomes the largest, is determined based on multiple image data obtained by successive image pickup operations performed by the image taking unit 1. Then, the index at the position associated with the state shown in FIG. 22B (the state in which observer is seeing infinity) is displayed on the image forming element 2 again. The observer is instructed to see the displayed index again, and an image of the eye 5 while observing is picked up. This state will be referred to as the first state.

Based on the image data obtained by the image pickup operation performed in the first state, both ends of the colored part of the eye are extracted, and the center of them is set as the pupil position.

With respect to the vertical direction, it is often the case that the upper and lower portions of the colored part are covered by the eyelid. Therefore, the portion covered by the eyelid is supplemented based on the radius of curvature of the curve of the colored part obtained by the image pickup operation, and the detection process same as the above-described process for the horizontal direction is performed.

Individual variations in the shift amount among observers who wear the HMD is larger in the vertical direction than in the horizontal direction. In this embodiment, it is assumed that the HMD that the observer wears is at a position near the position suitable for observation, and the vertical shift amount of the pupil position is detected based on the shift amount P shown in FIG. 21 to correct a small displacement.

Here, the resolution in detecting the pupil position depends on the resolution of the image taking unit 1. For example, if the pupil position is to be detected with 0.1 mm pitch, the horizontal resolution of the image taking unit 1 should be 300 (pixels) or more, since the image pickup range in the horizontal direction is set to 30 mm as described before. This also applies to the vertical resolution.

In this embodiment, it is assumed that the horizontal resolution of the image taking unit 1 is 600. The point of origin is set at the center of the image obtained by the image pickup operation, and the X coordinate is set in the range of ±300 and the Y coordinate is set in the range of ±200 as shown in FIG. 23.

Figure 23:
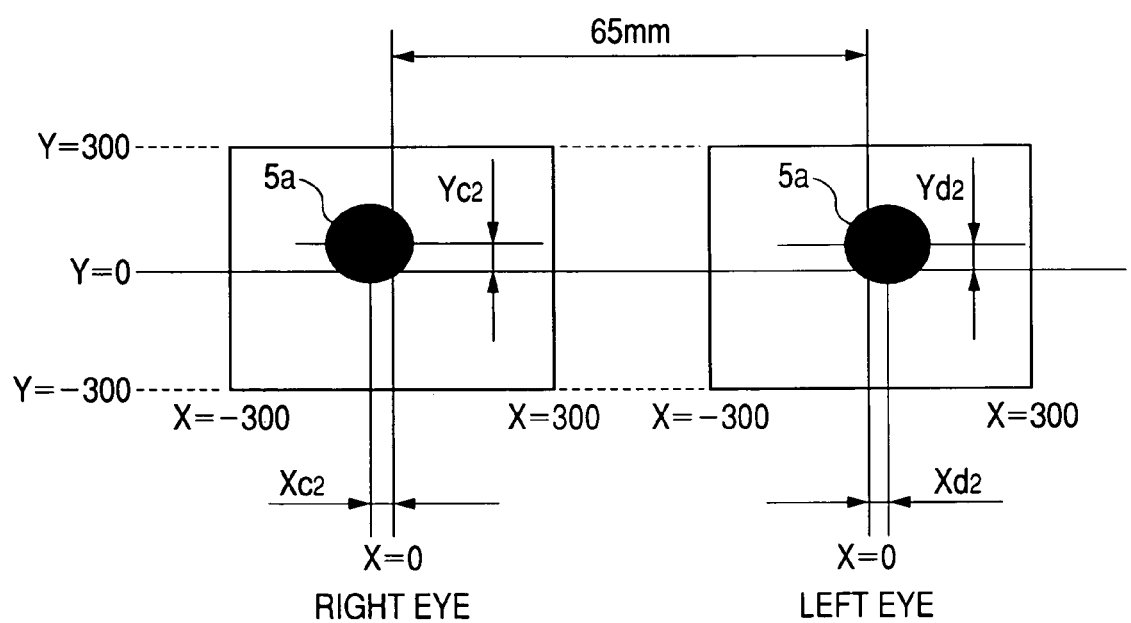
FIG. 23 is a diagram showing a shift amount of the pupil position in the fourth embodiment.

It is possible to determine the shift amount Xc2 in the X direction (horizontal direction) and the shift amount Yc2 in the Y direction (vertical direction) of the right eye, as shown in FIG. 23, using formula (1) presented in the description of the first embodiment. Shift amount Xc2 is the shift amount of the pupil position of the right eye in the X direction from the center of the image (X=0). Shift amount Yc2 is the shift amount of the pupil position of the right eye in the Y direction from the center of the image (Y=0).

Similarly, it is possible to determine the shift amount Xd2 in the X direction (horizontal direction) and the shift amount Yd2 in the Y direction (vertical direction) of the left eye, as shown in FIG. 23, using formula (1) presented in the description of the first embodiment. Shift amount Xd2 is the shift amount of the pupil position of the left eye in the X direction from the center of the image (X=0). Shift amount Yd2 is the shift amount of the pupil position of the left eye in the Y direction from the center of the image (Y=0).

The image of the eye obtained by the image pickup operation is an image under the state in which the eye 5 of the observer is at the position corresponding to the design value 20 mm of the eye relief. However, the eye of the observer is sometimes not at the desired eye relief position when he/she observes the display optical system 4. In such cases, the picked up image of the eye includes a magnification error, and the pupil position at that time may be displaced from the pupil position with the prescribed eye relief.

Therefore, it is necessary to correct the above-mentioned error (i.e. the magnification error). One method of correcting the magnification error is to move the image taking unit 1 in such a way that the distance between the eye 5 and the image taking unit 1 becomes larger than that before moving the image taking unit 1, in other words, to increase the optical path length as compared to that before moving the image taking unit 1 to enlarge the image pickup area. In the case where it is not possible to move the image taking unit 1 physically, the image pickup magnification may be changed to realize an optical effect equivalent to that realized by moving the image taking unit 1.

In this embodiment, the image taking unit 1 is moved away from the eye 5 by, for example, 10 mm so that the image pickup range at a distance of 30 mm from the display optical system 4 becomes 40 mm. Then, the index is displayed at the position same as that in the first state on the image forming element 2 to instruct the observer to see the index. This state will be referred to as the second state.

Then, an image pickup operation is performed in the second state. Shift amounts $Xc2'$ and $Xd2'$ are determined based on the images of the left and right eyes obtained by the image pickup operation performed in the second state using formula (1) presented in the description of the first embodiment. If the shift amounts $Xc2$ and $Xd2$ in the first state and the shift amounts in the second state $Xc2'$ and $Xd2'$ are different from each other, there should be a magnification error.

If there is a magnification error, shift amounts $Xc2''$ and $Xd2''$ in the actual observation state are determined using formula (2) presented in the description of the first embodiment, namely shift amounts with magnification error correction are determined. In the first state, measurement is performed in the state in which the center to center distance of the display optical systems 4 for the left and right eyes is set to 65 mm, it is possible to determine the interpupillary distance of the observer based on shift amount $Xc2''$ and shift amount $Xd2''$.

On the other hand, in cases where there is a magnification error with respect to the X direction, there also is a magnification error with respect to the Y direction. Therefore, shift amounts with magnification error correction for the Y direction, namely shift amounts $Yc2''$ and $Yd2''$ in the actual observation state are determined using formulas (1) and (2) in the same manner as in the determination of the shift amounts for the X direction.

By correcting the magnification error, it is possible to detect the correct shift amount of the emerging optical axis 7 of the display optical system 4 from the position of the pupil of the observer for each of the left and right eyes. Each display optical system 4 (or the display optical system and the image taking unit) is moved in the X and Y directions based on the detected shift amounts $Xc2''$ and $Yc2''$ or $Xd2''$ and $Yd2''$ in such a way that the optical axis position of the display optical-system 4 is substantially aligned with the pupil position. Thus, the observer can observe images displayed on the image forming element 2 without eclipse.

On the other hand, in this embodiment, images of the eye picked up while the observer is gazing at and following the index in the observer's pupil position detection process and index position information are associated with each other and stored in the memory circuit 9.

Since this data is for the initial state (the first state) of the display optical system 4, correction is made on the data based on the movement amounts of the display optical system 4 in the X and Y directions in order that the pupil position and the optical axis position of the display optical system are substantially aligned with each other.

Figure 21:
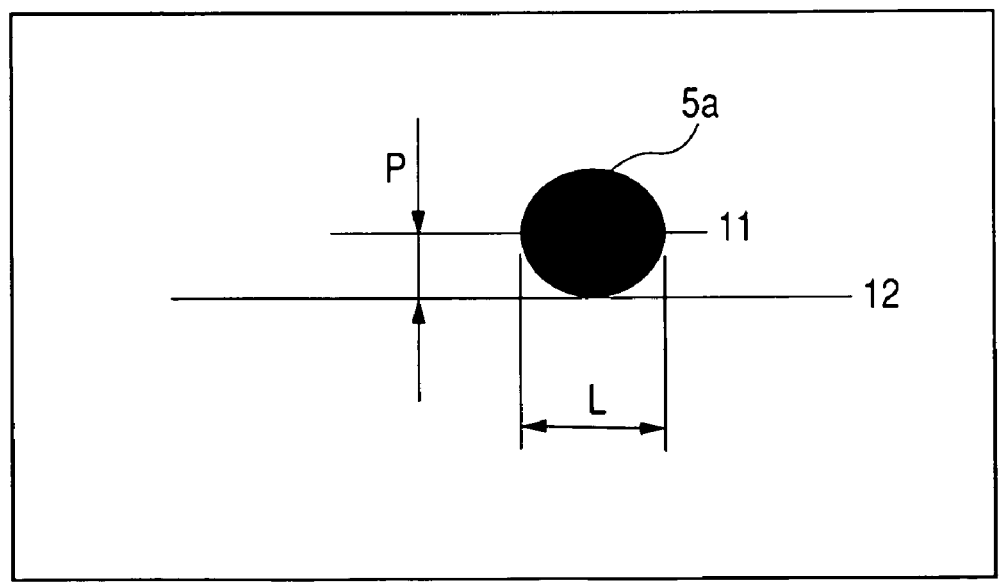
FIG. 21 shows a shift amount of the pupil position in the fourth embodiment.

After the pupil position and the optical axis position of the display optical system 4 have been substantially aligned with each other, image pickup of the eye of the observer is consecutively performed, and the width L of the colored part 5a and shift amount P shown in FIG. 21 are detected. It is possible to detect which position in the display area of the image forming element 2 the observer is gazing at with his/her left and right eyes by comparing the detected data and the above-described corrected data. Thus, it is possible to detect the point-of-gaze of the observer.

The image pickup of the eye is performed every time the observer wears the HMD, and the data in the memory circuit 9 is updated. Thus, it is possible to detect the point-of-gaze or the direction of the line of sight irrespective of individual variations such as variations in the size of the eyeball.

Then, the display optical system 4 is moved in such a way that the point-of-gaze or the direction of the line of sight thus detected is substantially aligned with the optical axis of the display optical system 4. Thus, the observer can observe images displayed on the image forming element 2 without eclipse.

The present invention can be applied to the mixed reality (MR) technology using an HMD. More specifically, the present invention can be applied to an HMD having the function of superimposing a virtual space on the real space directly observed through a mirror member or an HMD having the function of synthesizing a virtual space and the real space captured by a video camera.

This application claims priority from Japanese Patent Application No. 2004-295869 filed Oct. 8, 2004, which is hereby incorporated by reference herein.

The invention claimed is:

1. An image display apparatus comprising:
an eye detection apparatus;
an image forming unit that forms an image;
an optical unit that guides light from the image forming element to an eye of an observer; and
a drive unit mechanically linked to said optical unit, the drive unit moving at least part of said optical unit relative to said eye based on information from said eye detection apparatus,
wherein said eye detection apparatus comprises:
an image taking unit that picks up an image of an eye; and
a pupil detection unit that detects the position of the pupil in said eye based on a picked up image obtained by the image taking unit wherein the image taking unit determines said pupil position based on picked up images obtained in a plurality of states by said image taking unit.

2. An image display apparatus according to claim 1, wherein said plurality of states include states that are different from each other in the direction of the line of sight of said eye.

3. An image display apparatus according to claim 2, further comprising a display unit that displays an index for fixing said direction of the line of sight while changing the display position of the index.

4. An image display apparatus according to claim 3, further comprising a point-of-gaze detection unit that determines the position at which said eye gazes based on the display position of said index and said pupil position associated with the displayed position.

5. An image display apparatus according to claim 1, wherein said plurality of states include states that are different from each other in the position of said image taking unit relative to said eye with respect to the direction of an image taking optical axis.

6. An image display apparatus according to claim 1, wherein said plurality of states include states that are different from each other in the image taking magnification of said image taking unit.

7. An image display apparatus according to claim 1, wherein said plurality of states include states that are different from each other in the position of said image taking unit relative to said eye with respect to a direction orthogonal to an image taking optical axis.

8. An image display apparatus according to claim 1, further comprising an interpupillary distance detection unit for determining the distance of left and right eyes based on said pupil position in each of said left and right eyes determined by said pupil detection unit.

9. An image display apparatus according to claim 1 wherein said drive unit moves at least part of said optical unit in such a way that said pupil position and the position of the emerging optical axis of said optical unit substantially coincide with each other.

10. An image display apparatus according to claim 1, wherein the difference along a direction orthogonal to an image taking optical axis between said pupil position and a reference position in said picked up image determines the direction of the line of sight.

* * * * *

UNITED STATES PATENT AND TRADEMARK OFFICE
CERTIFICATE OF CORRECTION

PATENT NO. : 7,414,791 B2  Page 1 of 1
APPLICATION NO. : 11/245896
DATED : August 19, 2008
INVENTOR(S) : Takashi Urakawa, Yoshihiro Saito and Akinari Takagi It is certified that error appears in the above-identified patent and that said Letters Patent is hereby corrected as shown below:

<u>On the cover page, item (75) Inventor:</u>

Please replace "Yoshihiroi Saito" with --Yoshihiro Saito--.

Signed and Sealed this

Sixteenth Day of December, 2008

JON W. DUDAS
*Director of the United States Patent and Trademark Office*